United States Patent
Pascolo

(10) Patent No.: US 10,626,400 B2
(45) Date of Patent: Apr. 21, 2020

(54) STABILISED FORMULATIONS OF RNA

(71) Applicant: BIONTECH AG, Mainz (DE)

(72) Inventor: Steve Pascolo, Zürich (CH)

(73) Assignee: BioNTech AG, Mainz (DE)

( * ) Notice: Subject to any disclaimer, the term of this patent is extended or adjusted under 35 U.S.C. 154(b) by 0 days.

(21) Appl. No.: 15/323,599

(22) PCT Filed: Jul. 4, 2014

(86) PCT No.: PCT/EP2014/064335
§ 371 (c)(1),
(2) Date: Jan. 3, 2017

(87) PCT Pub. No.: WO2016/000792
PCT Pub. Date: Jan. 7, 2016

(65) Prior Publication Data
US 2017/0136129 A1    May 18, 2017

(51) Int. Cl.
*C12N 15/117* (2010.01)
*A61K 47/26* (2006.01)
*A61K 9/00* (2006.01)
*A61K 47/64* (2017.01)
*A61K 47/69* (2017.01)
*A61K 39/39* (2006.01)
*A61K 48/00* (2006.01)
*A61K 39/00* (2006.01)

(52) U.S. Cl.
CPC .......... *C12N 15/117* (2013.01); *A61K 9/0019* (2013.01); *A61K 39/39* (2013.01); *A61K 47/26* (2013.01); *A61K 47/6455* (2017.08); *A61K 47/6931* (2017.08); *A61K 48/0041* (2013.01); *A61K 2039/55561* (2013.01); *C12N 2310/17* (2013.01); *C12N 2310/351* (2013.01); *C12N 2320/32* (2013.01)

(58) Field of Classification Search
None
See application file for complete search history.

(56) References Cited

U.S. PATENT DOCUMENTS

| | | | |
|---|---|---|---|
| 2008/0267873 A1† | 10/2008 | Hoerr | |
| 2009/0042829 A1 | 2/2009 | Matar et al. | |
| 2011/0237645 A1* | 9/2011 | Sluka | A61K 31/7105 514/44 A |

FOREIGN PATENT DOCUMENTS

| WO | WO-03/106636 A2 | 12/2003 |
|---|---|---|
| WO | WO-2004/028560 A1 | 4/2004 |
| WO | WO-2008/054544 A2 | 5/2008 |
| WO | WO-2009/036368 A2 | 3/2009 |
| WO | 2009144230 A1 † | 12/2009 |
| WO | WO-2009/144230 A1 | 12/2009 |
| WO | WO-2009/144481 A2 | 12/2009 |
| WO | 2011069586 A1 † | 6/2011 |
| WO | WO-2011/069529 A1 | 6/2011 |
| WO | WO-2014/133351 A1 | 9/2014 |
| WO | WO-2016/000792 A1 | 1/2016 |

OTHER PUBLICATIONS

Rettig, L. et al., Particle Size and Activation Threshold: a New Dimension of Danger Signaling. Blood. 2010; 115(22):4533-41.
International Search Report and Written Opinion dated Mar. 12, 2015 by the International Searching Authority for International Patent Application No. PCT/EP2014/064335, which was filed on Jul. 4, 2014 and published as WO 2016/000792 on Jan. 7, 2016 (Inventor—Pascolo et al.; Applicant—Biontech AG) (9 pages).
International Preliminary Report on Patentability dated Jan. 10, 2017 by the International Searching Authority for International Patent Application No. PCT/EP2014/064335, which was filed on Jul. 4, 2014 and published as WO 2016/000792 on Jan. 7, 2016 (Inventor—Pascolo et al.; Applicant—Biontech AG) (6 pages).
PCT, PCT/EP2014/064335 (WO 2016/000792), Jul. 4, 2014 (Jan. 7, 2016), Biontech AG.
Fotin-Mleczek et al., "Messenger RNA-based vaccines with dual activity induce balanced TLR-7 dependent adaptive immune responses and provide antitumor activity," J Immunother., 34(1):1-15, 2011.†
Fotin-Mleczek et al., "Messenger RNA-based vaccines with dual activity induce balanced TLR-7 dependent adaptive immune responses and provide antitumor activity," J Immunother., 34(1):1-15, 2001.†

\* cited by examiner
† cited by third party

*Primary Examiner* — J. E Angell
(74) *Attorney, Agent, or Firm* — Ballard Spahr LLP

(57) ABSTRACT

The present invention relates to stable low-salt aqueous formulations of particles comprising a polycation, preferably protamine, and RNA, which formulations are preferably isotonic, to pharmaceutical compositions or kits comprising such formulations and to their use in medicine. It further relates to methods for preparing the formulations of the invention and to methods for physically stabilizing particles comprising a polycation, preferably protamine, and RNA.

10 Claims, 8 Drawing Sheets

STABILISED FORMULATIONS OF RNA

CROSS REFERENCE TO RELATED APPLICATION

The application is a National Phase Under 35 U.S.C. § 371 of International Application No. PCT/EP2014/064335 filed on Jul. 4, 2014, which is herein incorporated by reference.

TECHNICAL FIELD OF THE INVENTION

The present invention relates to stable low-salt aqueous formulations of particles comprising a polycation, preferably protamine, and RNA, which formulations are preferably isotonic, to pharmaceutical compositions or kits comprising such formulations and to their use in medicine. It further relates to methods for preparing the formulations of the invention and to methods for physically stabilizing particles comprising a polycation, preferably protamine, and RNA.

BACKGROUND OF THE INVENTION

Exogenous RNA can be delivered into cells by way of vectorization, for example using natural polycationic peptides termed protamine. The inventor has previously shown that under specific conditions protamine and RNA can form nanoparticles, termed protamine-RNA particles, which can deliver RNA into cells, particularly into cell compartments (e.g. endosomes) where immune sensors of infections, such as Toll-Like Receptors (TLRs) 7 and 8 are located (Rettig L. et al., 2010, Blood 115(22):4533-41 and WO 2009/144230 A1). The particles may activate TLR-7 when taken up by, for example, plasmacytoid dendritic cells, or TLR-8 when taken up by, for example, monocytes. In addition, at best when they are smaller than 450 nm, the particles can deliver their RNA content into the cytosol and thereby allow, for example, protein expression in case the RNA entrapped in the protamine particles is a coding RNA, such as messenger RNA (mRNA).

However, the present inventor observed that the protamine-RNA nanoparticles, particularly those below 450 nm, are unstable, e.g. enlarge over time, when diluted in salty pharmaceutical carriers, such as 0.9% saline, Ringer or Ringer Lactate. As a consequence, they lose their physical characteristics (e.g. size) and associated biological properties (e.g. specific immunostimulating features or cytosolic release of the entrapped RNA) when formulated for injection, i.e. in isotonic salty solution.

Accordingly, it was an object of the present invention to provide aqueous formulations of particles comprising a polycation, such as protamine, and RNA that are characterized by an increased physical stability of the particles contained therein and can be used for injection.

SUMMARY OF THE INVENTION

In a first aspect, the present invention relates to an aqueous formulation comprising:
 particles comprising a polycation and RNA and
 a non-electrolyte osmotic agent,
wherein the aqueous formulation comprises less than 50 mM electrolytes.

In one embodiment, the aqueous formulation comprises less than 25 mM electrolytes, preferably less than 15 mM electrolytes.

In one embodiment, the polycation is selected from the group consisting of polycationic polymers and polycationic peptides.

In one embodiment, the polycation is protamine.

In one embodiment, the non-electrolyte osmotic agent is a sugar.

In one embodiment, the aqueous formulation comprises 1 to 20% (w/v), preferably 1 to 10% (w/v), more preferably 3 to 7% (w/v), even more preferably 4 to 6% (w/v), even more preferably 5% (w/v) of the sugar.

In one embodiment, the sugar is selected from the group consisting of glucose, fructose and mannose.

In one embodiment, the non-electrolyte osmotic agent is present in amount so as to provide an isotonic aqueous formulation.

In one embodiment, the non-electrolyte osmotic agent is glucose, wherein, preferably, the aqueous formulation comprises 5% (w/v) of glucose.

In one embodiment, the particles have a polycation:RNA mass ratio in the range of from 16:1 to 1:2, preferably in the range of from 8:1 to 1:2, more preferably in the range of from 4:1 to 1:2.

In one embodiment, the particles have a size in the range of from 10 to 990 nm, preferably in the range of from 10 to 750 nm, more preferably in the range of from 10 to 450 nm.

In one embodiment, the RNA is selected from the group consisting of messenger RNA (mRNA), transfer RNA (tRNA), ribosomic RNA (rRNA), small nuclear RNA (snRNA), small inhibitory RNA (siRNA), small hairpin RNA (shRNA), microRNA (miRNA), antisense RNA, immunostimulating RNA (isRNA) and RNA aptamers, preferably from the group consisting of mRNA, siRNA, shRNA, miRNA, antisense RNA, isRNA and RNA aptamers.

In one embodiment, the aqueous formulation is suitable for parenteral administration.

In another aspect, the present invention relates to a pharmaceutical composition or kit comprising the aqueous formulation according to the present invention.

In a further aspect, the present invention relates the aqueous formulation according to the present invention or the pharmaceutical composition or kit according to the present invention for use in a method of treatment or prevention of a disease or for use in a method of immunostimulation.

In yet another aspect, the present invention relates to a method for preparing an aqueous formulation comprising particles comprising a polycation and RNA, the method comprising the steps of:
 (a) providing an aqueous solution of the RNA;
 (b) providing an aqueous solution of the polycation;
 (c) providing an aqueous 2 to 40% (w/v) solution of a non-electrolyte osmotic agent; and
 (d) combining and, preferably, mixing the aqueous solutions obtained in steps (a) and (b) and adding the aqueous solution obtained in step (c),
wherein the aqueous formulation comprises less than 50 mM electrolytes.

In a further aspect, the present invention relates to a method for preparing an aqueous formulation comprising particles comprising a polycation and RNA, the method comprising the steps of:
 (a) providing an aqueous solution of the RNA and 1 to 20% (w/v) of a non-electrolyte osmotic agent;
 (b) providing an aqueous solution of the polycation and 1 to 20% (w/v) of the non-electrolyte osmotic agent; and
 (c) combining and, preferably, mixing the aqueous solutions obtained in steps (a) and (b), wherein the aqueous formulation comprises less than 50 mM electrolytes.

In one embodiment of the above methods, the aqueous formulation comprises less than 25 mM electrolytes, preferably less than 15 mM electrolytes.

In one embodiment of the above methods, the polycation is protamine.

In one embodiment of the above methods, the non-electrolyte osmotic agent is a sugar, preferably glucose.

In one embodiment of the above methods, the concentration of the RNA in the aqueous solution provided in step (a) and/or the concentration of the polycation in the aqueous solution provided in step (b) is less than 5 mg/ml, preferably 1.5 mg/ml or less, more preferably 1 mg/ml or less.

In one embodiment of the above methods, the non-electrolyte osmotic agent is present in amount so as to provide an isotonic aqueous formulation.

In another aspect, the present invention relates to a kit comprising RNA, a polycation, and a non-electrolyte osmotic agent in separate containers and further comprising instructions for use of the kit in a method as defined above.

In one embodiment, the polycation is protamine.

In one embodiment, the non-electrolyte osmotic agent is a sugar, preferably glucose.

In yet another aspect, the present invention relates to a method for physically stabilizing particles comprising a polycation and RNA, the method comprising formulating the particles in an aqueous formulation comprising a non-electrolyte osmotic agent and less than 50 mM electrolytes.

In one embodiment, physically stabilizing comprises reducing or preventing enlargement of the particles over time.

In one embodiment, the aqueous formulation comprises less than 25 mM electrolytes, preferably less than 15 mM electrolytes.

In one embodiment, the polycation is protamine.

In one embodiment, the non-electrolyte osmotic agent is a sugar, preferably glucose.

DESCRIPTION OF THE DRAWINGS

Other objects, advantages and novel features of the present invention will become apparent from the following detailed description when considered in conjunction with the accompanying drawings.

It is demonstrated that nanoparticles of an average size of less than 200 nm are formed by the combination of protamine and RNA and that those particles are stable in water or in a glucose solution but not in a salty (PBS) solution. In the salty solution, particles get larger over time, possibly through aggregation of nanoparticles.

Figure 2A:
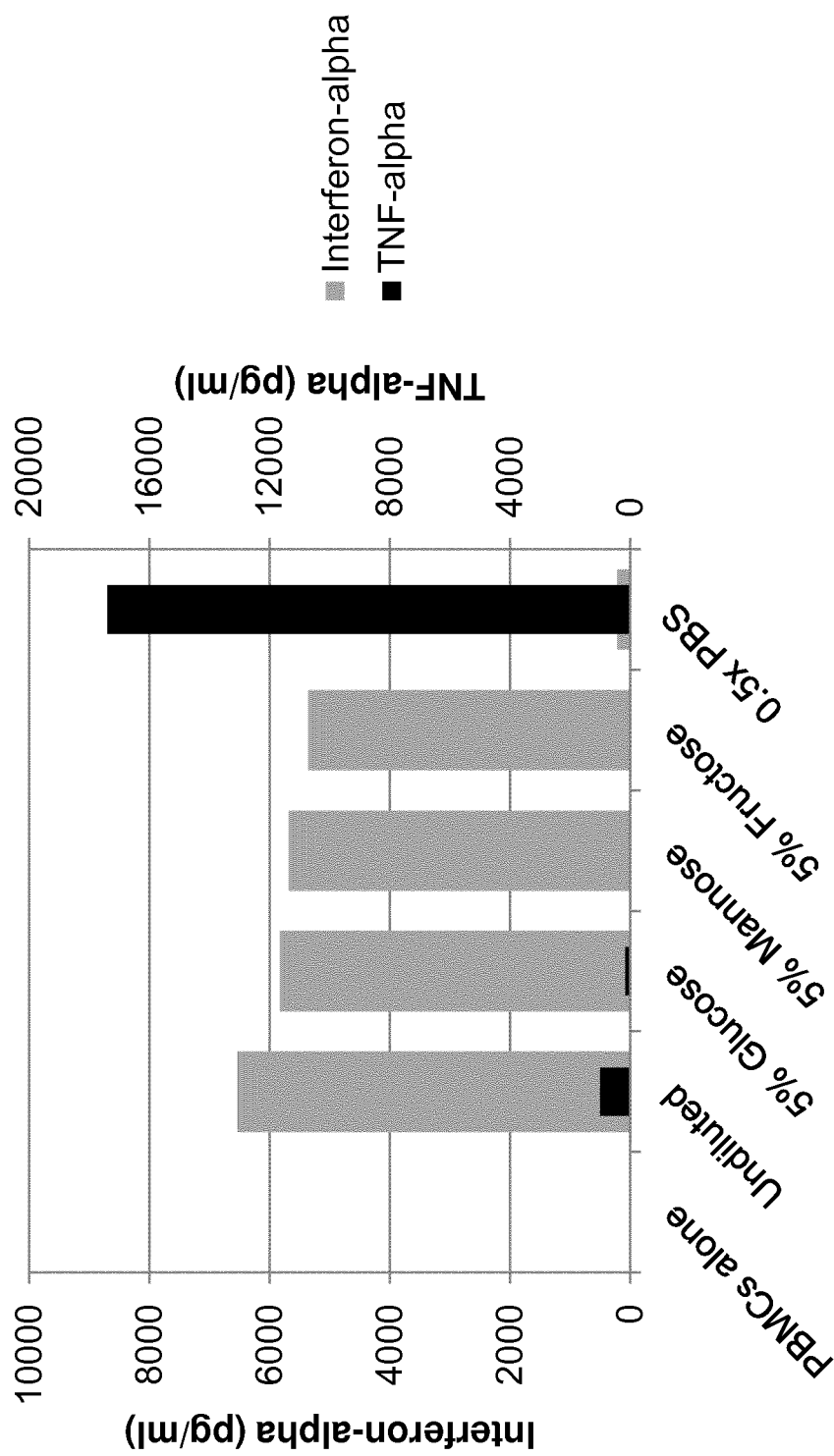
Figure 2B:
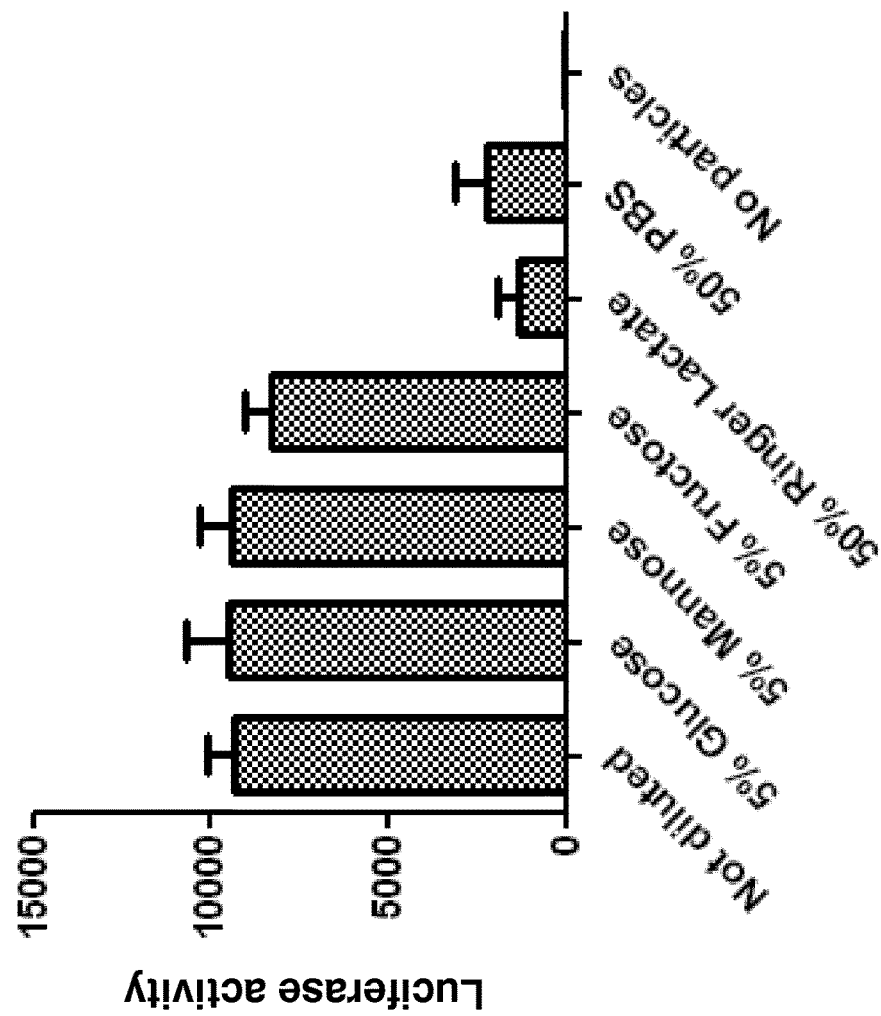

FIG. 2: Specific functionalities of protamine-RNA nanoparticles are preserved in non-salty sugar solutions but modified in salty solutions 50 micrograms of mRNA coding for firefly luciferase were diluted to 0.5 mg/ml in deionized water and mixed with 100 micrograms of protamine (Protamin® IPEX 5000) diluted to 0.5 mg/ml in pure water. The mixture was incubated at room temperature for 10 minutes. This formulation generates particles with an average size of approximately 120 nm as measured by light scattering spectroscopy.

Figure 1:
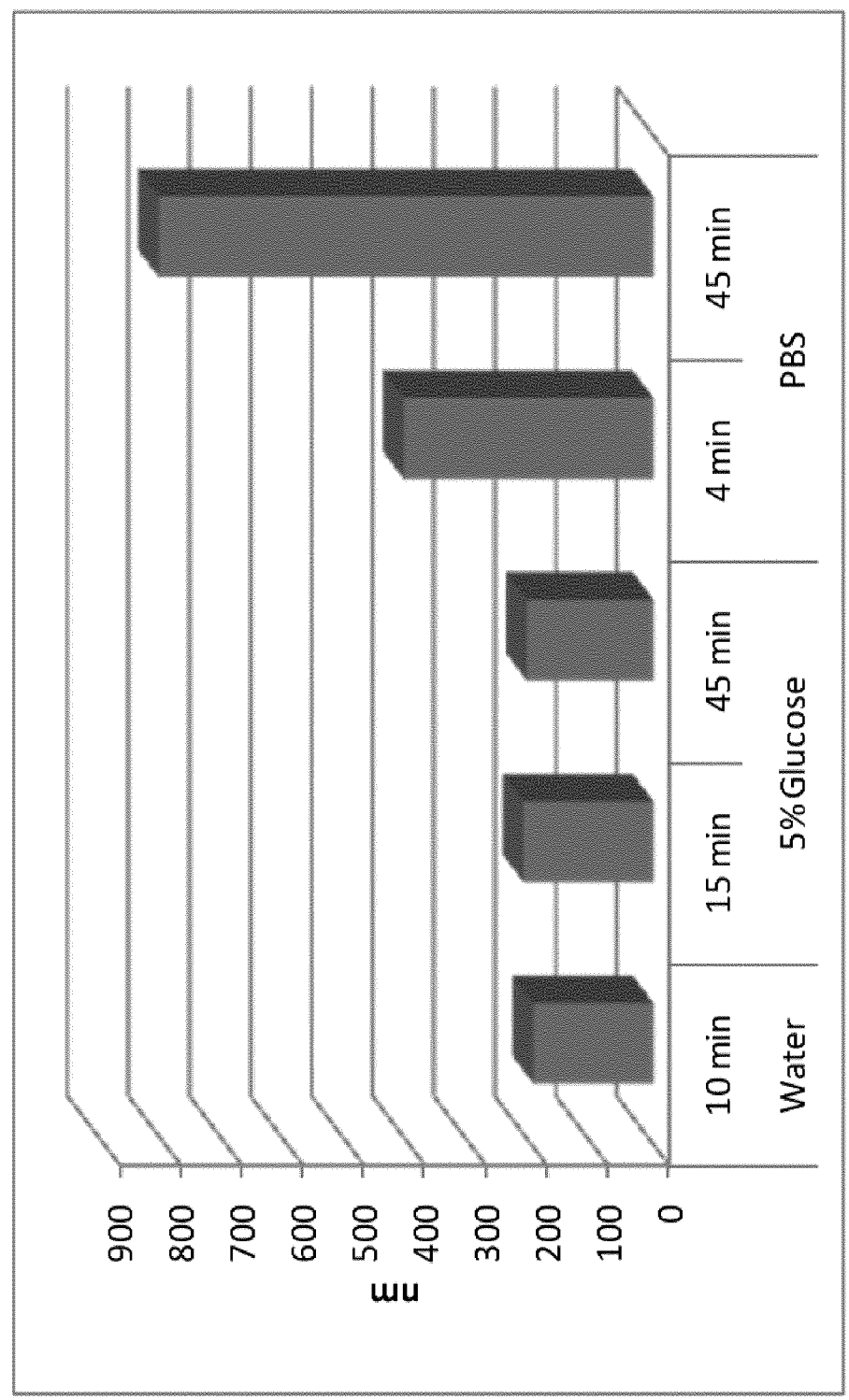
FIG. 1: Adding glucose solutions but not salty solutions to protamine-RNA nanoparticles allows to maintain particle size RNA (mRNA coding for firefly luciferase) and protamine were diluted to 1 mg/ml using deionized water (also referred herein as "pure water"). Five micrograms RNA (5 microliters) were mixed with 10 micrograms Protamin® IPEX (10 microliters). The mix was incubated 10 min at room temperature and then diluted with either:
- 1 ml of water; particle size was measured 10 minutes later using light scattering spectroscopy ("10 min Water");
- 1 ml of 5% D-glucose ("5% glucose"); particle size was measured 15 or 45 minutes later using light scattering spectroscopy ("15 min" or "45 min", respectively); or
- 1 ml of phosphate buffered saline ("PBS"); particle size was measured 4 or 45 minutes later using light scattering spectroscopy ("4 min" or "45 min", respectively).

In A, 3 microliters of the protamine-RNA solution (i.e. 0.5 micrograms of RNA mixed with 1 microgram of protamine) were distributed to wells of a 96-well U bottom plate. Then, eventually 3 microliters of 10% sugar solutions or PBS were added. The mixtures were left 10 minutes at room temperature and then two hundred microliters (1 million of cells) of human peripheral blood mononuclear cells (PBMCs obtained by centrifugation of fresh human blood on a ficoll solution) in complete culture medium (RPMI containing 10% fetal calf serum, glutamine and penicillin/streptomycin) were added. As negative control, PBMCs were cultured alone. After 18 hours at 37° C. in a humidified atmosphere containing 5% $CO_2$, the amount of interferon-alpha and TNF-alpha produced by cells was evaluated using 20 microliters and 10 microliters, respectively, of culture supernatants and the Mabtech pan-interferon-alpha or Biolegend TNF-alpha kit, respectively. Protamine-RNA particles induce particularly interferon-alpha in PBMCs when they are less than 450 nm and TNF-alpha when they are more than 450 nm in size. In line with their small size, the formulated undiluted particles of 120 nm induced as expected interferon-alpha and no TNF-alpha production. The immunostimulating activity of particles diluted with sugar solutions (glucose, mannose or fructose) was identical to the one of undiluted particles (production of interferon-alpha but not of TNF-alpha). Thus, particles are stable in sugar solutions having an osmolarity close to the one of serum (approximately 300 mOsm/L). On the contrary, particles left 10 minutes in salty solutions (e.g., 0.5×PBS) before addition of PBMCs induce TNF-alpha and no interferon-alpha, indicating, as also shown in FIG. 1, that their size increases to more than 450 nm.

In B, 6 microliters of the protamine-RNA solution (i.e. 1 microgram of RNA mixed with 2 micrograms of protamine) were distributed to wells of a flat bottom white 96-well plate. Then, eventually 6 microliters of 10% sugar solutions or PBS or Ringer Lactate were added. The mixtures were left 10 minutes at room temperature and then one hundred microliters (0.2 million of cells) of HEK cells in complete culture medium (RPMI containing 10% fetal calf serum, glutamine and penicillin/streptomycin) were added. As negative control, HEK cells were cultured alone ("No particles"). After 18 hours at 37° C. in a humidified atmosphere containing 5% $CO_2$, the production of luciferase by cells was evaluated by adding 75 microliters of Bright Glo™ (Promega) in each well and measuring light emission using a luminometer. The results are given as mean and variation values of triplicates. They show that undiluted particles ("Not diluted") of less than 450 nm are capable to deliver translatable mRNA into HEK cells. This feature is preserved when particles are diluted in sugar solutions ("5% glucose", "5% mannose", "5% fructose") but reduced when particles are diluted in salty solutions (e.g., 50% PBS or 50% Ringer Lactate final). Thus, mRNA expression after pulsing tumor cells with protamine-RNA particles is optimal when particles are preserved in their size below 450 nm (undiluted or diluted in tonic sugar-based solutions providing osmolarity close to physiological tonicity, i.e. approx. 300 mOsm/L) but impaired when particle size is increased, as it is the case when 120 nm protamine-RNA particles are diluted in salty solutions. All tested sugars allow to maintain optimal translatability of small (approximately 120 nm) protamine-RNA nanoparticles.

Figure 3A:
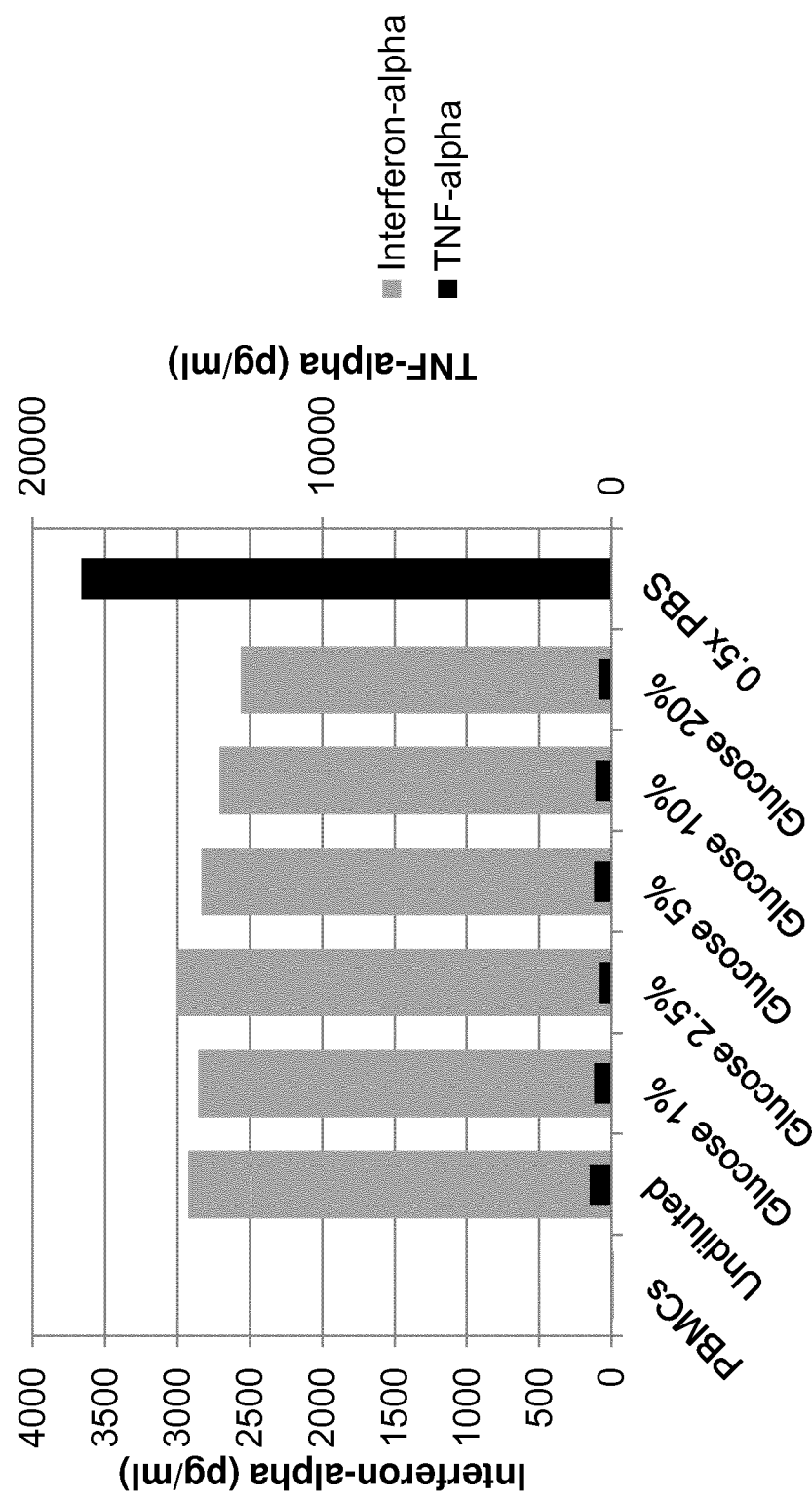
Figure 3B:
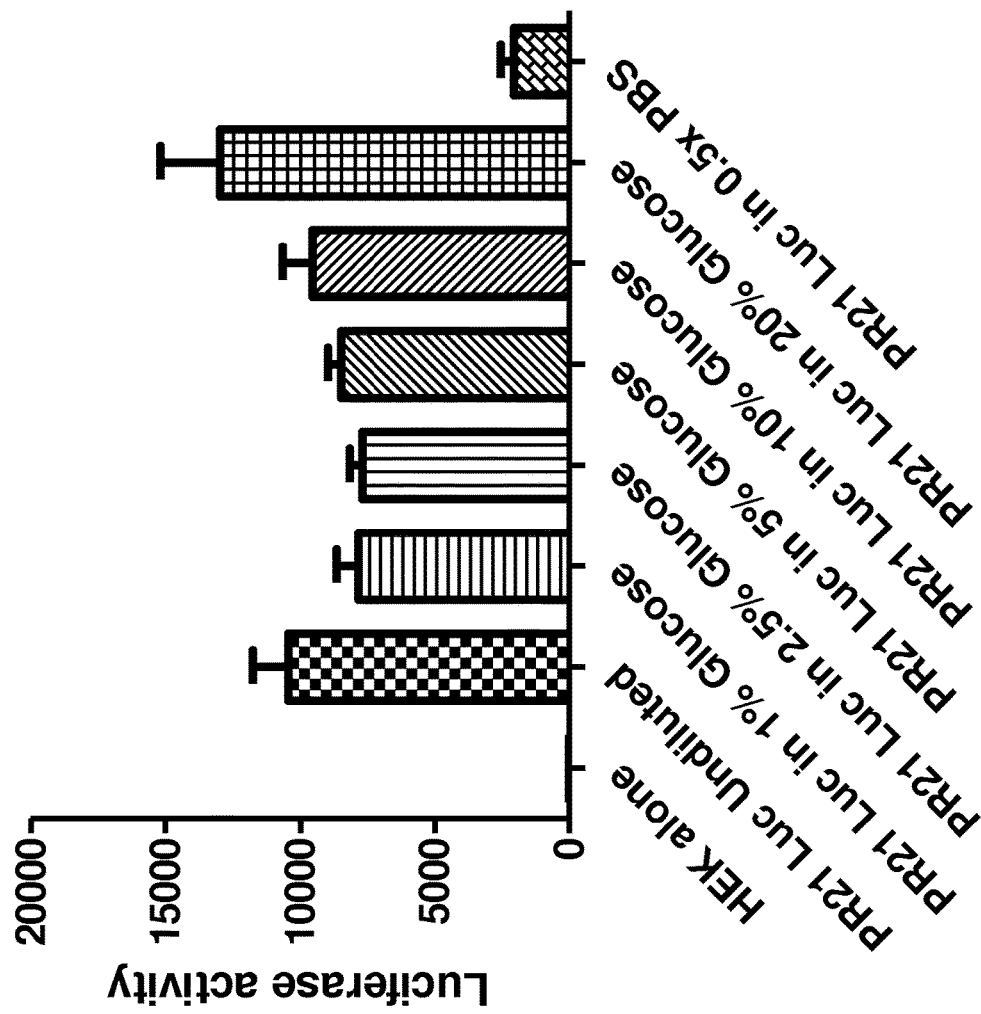

FIG. 3: Specific functionalities of nanoparticles are preserved in non-salty 1% to 20% sugar solutions 50 micrograms of mRNA coding for firefly luciferase were diluted to 0.5 mg/ml in pure water and mixed with 100 micrograms of protamine (Protamin® IPEX 5000) diluted to 0.5 mg/ml in pure water. The mixture was incubated at room temperature for 10 minutes. This formulation generates particles with an average size of approximately 120 nm as measured by light scattering spectroscopy.

In A, 3 microliters of the protamine-RNA solution (i.e. 0.5 micrograms of RNA mixed with 1 microgram of protamine) were distributed to wells of a 96-well U bottom plate. Then, eventually 3 microliters of glucose solutions at 2%, 5%, 10%, 20% or 40% (weight/volume) or PBS were added. The mixtures were left for 10 minutes at room temperature and then two hundred microliters (1 million of cells) of human peripheral blood mononuclear cells (PBMCs obtained by centrifugation of fresh human blood on a ficoll solution) in complete culture medium (RPMI containing 10% fetal calf serum, glutamine and penicillin/streptomycin) were added. As negative control, PBMCs were cultured alone ("PBMCs"). After 18 hours at 37° C. in a humidified atmosphere containing 5% $CO_2$, the amount of interferon-alpha and TNF-alpha produced by cells was evaluated using 20 microliters and 10 microliters, respectively, of culture supernatants and the Mabtech pan-interferon-alpha or Biolegend TNF-alpha kit, respectively. Protamine-RNA particles induce preferentially interferon-alpha in PBMCs when they are less than 450 nm and TNF-alpha when they are more than 450 nm in size. In line with their size below 450 nm, the formulated undiluted particles ("Undiluted") induce as expected interferon-alpha and no TNF-alpha production. The immunostimulating activity of particles diluted with glucose solutions to final concentrations of 1%, 2.5%, 5%, 10% or 20% is identical to the one of undiluted particles (production of interferon-alpha but not of TNF-alpha). Thus, all tested glucose concentrations preserve the size (i.e. the physical stability) of the particles. On the contrary, particles left 10 minutes in a salty solution ("0.5×PBS") before addition of PBMCs induce TNF-alpha and no interferon-alpha, indicating, as also shown in FIG. 1, that their size increases in the presence of salts, possibly by precipitating to particles of more than 450 nm.

In B, 6 microliters of the protamine-RNA solution (i.e. 1 microgram of RNA mixed with 2 micrograms of protamine) were distributed to wells of a flat bottom white 96-well plate. Then, eventually 6 microliters of glucose solutions at 2%, 5%, 10%, 20% or 40% (weight/volume) or PBS were added. The mixtures were left 10 minutes at room temperature and then one hundred microliters (0.2 million of cells) of HEK cells in complete culture medium (RPMI containing 10% fetal calf serum, glutamine and penicillin/streptomycin) were added. As negative control, HEK cells were cultured alone ("HEK alone"). After 18 hours at 37° C. in a humidified atmosphere containing 5% $CO_2$, the production of Luciferase by cells was evaluated by adding 75 microliters of Bright Glo™ (Promega) in each well and measuring light emission using a luminometer. The results are given as mean and variation values of triplicates. As their average size is below 450 nm, undiluted particles ("PR21 Luc Undiluted") are delivering translatable mRNA to HEK cells. This feature was preserved when particles are diluted in glucose solutions of 1% to 20% ("PR21 Luc in 1% glucose", "PR21 Luc in 2.5% glucose", "PR21 Luc in 5% glucose", "PR21 Luc in 10% glucose", "PR21 Luc in 20% glucose") but impaired when particles are diluted in salty solutions such as PBS ("PR21 Luc in 0.5×PBS"). Thus, mRNA expression after pulsing tumor cells with protamine-RNA particles is optimal when particles have an average size below 450 nm but reduced when particles are larger, as it is the case when 120 nm protamine-RNA particles are incubated in salty solutions. All tested concentrations of D-glucose allow to maintain the optimal translatability feature of small (approximately 120 nm in average) protamine-RNA nanoparticles.

FIG. 4: Small stable protamine-RNA nanoparticles in isotonic formulations (approximately 300 mOsm/L solution) can be obtained by diluting RNA and Protamine in 5% glucose before mixing them In A, light scattering spectroscopy measurement of particles made from: (upper panel) 8 micrograms of mRNA encoding luciferase diluted at 0.5 mg/ml in water mixed with 16 micrograms of Protamin® IPEX 5000 diluted at 0.5 mg/ml in water (after 10 minutes, volume is filled up to 200 microliters using 152 microliters of 5% glucose); or (lower panel) 8 micrograms of mRNA encoding luciferase diluted at 0.5 mg/ml in 5% glucose mixed with 16 micrograms of Protamin® IPEX diluted at 0.5 mg/ml in 5% glucose (after 10 minutes, volume is filled up to 200 microliters using 152 microliters of 5% glucose). The size of particles made by mixing RNA and protamine diluted to 0.5 mg/ml in water or RNA and protamine diluted to 0.5 mg/ml in 5% glucose is similar. Thus, protamine-RNA particles in solutions approaching serum osmolarity (approximately 300 mOsm/L) can be obtained by either adding glucose in particles formed by mixing reagents diluted in water or by diluting reagents (protamine and RNA) in 5% glucose before mixing them.

In B, 8 micrograms of mRNA coding for firefly luciferase were diluted to 0.5 mg/ml in pure water or in 5% glucose or in PBS and mixed with 16 micrograms of protamine (Protamin® IPEX 5000) diluted to 0.5 mg/ml in pure water or in 5% glucose or in PBS. Water-diluted reagents were mixed together generating "Water" particles, glucose-diluted reagents were mixed together generating "glucose" particles and PBS-diluted reagents were mixed together generating "PBS" particles. The mixtures were all incubated at room temperature for 10 minutes. Then, they were distributed to wells of a U-bottom 96-well plate (3 microliters per well equivalent to 0.5 micrograms RNA and 1 microgram protamine) before two hundred microliters (1 million of cells) of human peripheral blood mononuclear cells (PBMCs obtained by centrifugation of fresh human blood on a ficoll solution) in complete culture medium (RPMI containing 10% fetal calf serum, glutamine and penicillin/streptomycin) were added. As negative controls, PBMCs were cultured alone ("PBMCs alone") or in the presence of 1 microgram of protamine ("Protamine alone"). After 18 hours at 37° C. in a humidified atmosphere containing 5% $CO_2$, the amount of interferon-alpha and TNF-alpha produced by cells was evaluated using 20 microliters and 10 microliters, respectively, of culture supernatants and the Mabtech pan-interferon-alpha or Biolegend TNF-alpha kit, respectively. "Water" and "Glucose" particles triggered predominantly interferon-alpha production in PBMCs, a feature of immunomodulation by small protamine-RNA nanoparticles of less than 450 nm. On the contrary, "PBS" particles triggered predominantly TNF-alpha production in PBMCs, a feature of immunomodulation by large protamine-RNA nanoparticles of more than 450 nm.

In C, 8 micrograms of mRNA coding for firefly luciferase were diluted to 0.5 mg/ml in pure water or in 5% glucose and mixed with 16 micrograms of protamine (Protamin® IPEX 5000) diluted to 0.5 mg/ml in pure water or in 5% glucose. Water-diluted reagents were mixed together generating "Water" particles and glucose-diluted reagents were mixed together generating "Glucose 5%" particles. The mixtures were all incubated at room temperature for 10 minutes. Then they were distributed to wells of a flat-bottom white 96-well plate (6 microliters per well equivalent to 1 microgram RNA and 2 micrograms protamine) before one hundred microliters (0.2 million of cells) of HEK cells in complete culture medium (RPMI containing 10% fetal calf serum, glutamine and penicillin/streptomycin) were added. As negative control, HEK cells were cultured alone ("HEK alone"). After 18 hours at 37° C. in a humidified atmosphere containing 5% $CO_2$, the production of luciferase by cells was evaluated by adding 75 microliters of Bright Glo™ (Promega) in each well and measuring light emission using a luminometer. The results are given as mean and variation values of triplicates. Particles made from reagents diluted in pure water or in 5% glucose allow transfection of HEK cells and expression of luciferase which is at its optimum when protamine-RNA particles are below 450 nm.

Altogether, these biological assays correlate with the particle size analysis and demonstrate that small (below 450 nm) and functional (induction of interferon-alpha in PBMCs, expression of the protein encoded by the mRNA) protamine-RNA nanoparticles can be obtained when protamine and RNA are diluted in pure water or in 5% glucose before being mixed together.

DETAILED DESCRIPTION OF THE INVENTION

In the following, definitions will be provided which apply to all aspects of the present invention.

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Preferably, the terms used herein are defined as described in "A multilingual glossary of biotechnological terms: (IUPAC Recommendations)", H. G. W. Leuenberger, B. Nagel, and H. Kölbl, Eds., (1995) Helvetica Chimica Acta, CH-4010 Basel, Switzerland. The practice of the present invention will employ, unless otherwise indicated, conventional methods of biochemistry, cell biology, immunology, and recombinant DNA techniques which are explained in the literature in the field (cf., e.g., *Molecular Cloning: A Laboratory Manual*, $2^{nd}$ Edition, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps although in some embodiments such other member, integer or step or group of members, integers or steps may be excluded, i.e. the subject-matter consists in the inclusion of a stated member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein.

All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

The terms "aqueous formulation" and "aqueous solution", as used herein, refer to a formulation or solution in which the solvent is water or comprises water. The water used for an aqueous formulation or solution according to the present invention is preferably sterile and/or distilled or deionized. In one embodiment, the water is water for injection (WFI).

Preferably, particles comprising a polycation and RNA have a size in the range of from 10 nm to 990 nm, preferably of from 30 nm to 990 nm, more preferably of from 50 nm to 990 nm. In another embodiment, the particles have a size in the range of from 10 nm to 750 nm, preferably of from 10 nm to 450 nm, more preferably of from 30 nm to 450 nm, even more preferably of from 50 nm to 450 nm. In yet another embodiment, the particles have a size in the range of from 450 nm to 990 nm.

The term "size" refers to the average size of the particles and is generally the "design size" or intended size of the particles prepared according to an established process. Size may be a directly measured dimension, such as the average or maximum diameter, or may be determined by an indirect assay such as a filtration screening assay. Direct measurement of particle size is typically carried out by dynamic light scattering. As minor variations in size arise during the manufacturing process, a variation up to 40% of the stated measurement is acceptable and considered to be within the stated size. Alternatively, particle size may be determined by filtration screening assays. For example, a particle preparation is less than a stated size, if at least 97% of the particles pass through a "screen-type" filter of the stated size.

In accordance with the present invention, the particles may further comprise on their outer surface a targeting agent which can selectively or preferably deliver the particles to a target cell population, and/or to a target organ or tissue. Such targeting may promote efficient drug uptake into cells and enhance efficacy. One targeting means which has been explored employs antibodies attached covalently or through electrostatic interactions to particle surfaces. Thus, in one embodiment, the particles may comprise a ligand for site specific targeting, such as an antibody. The ligand may be capable of binding to a disease-associated antigen such that the particle when administered accumulates at a diseased organ or tissue characterized by cells expressing the disease-associated antigen and preferably being characterized by association of the disease-associated antigen with their cell surface, e.g. the disease-associated antigen is a transmembrane protein. The disease-associated antigen may be a tumor-associated antigen and is preferably associated with the surface of a diseased cell, such as a tumor cell but preferably not with the surface of a healthy cell. Preferably the ligand for site specific targeting binds to an extracellular portion of the disease-associated antigen.

In one embodiment, the particles further comprise an agent enhancing their bioavailability and/or bioactivity. In a particular embodiment, the particles are coated with polyethylene glycol (PEG).

In one embodiment, the aqueous formulation and/or the particles contained therein further comprise one or more endosome destabilizing agents (EDAs), which, preferably, facilitate the delivery of the particles and/or of any other component included in the aqueous formulation (e.g., an additional therapeutic agent as described herein, such as a free, i.e. non-particle bound, mRNA molecule) to the cytosol. The term "endosome destabilizing agent (EDA)", as used herein, refers to an agent having an "endosome destabilizing activity", wherein such "endosome destabilizing activity" may be based on a mechanism such as destabilization of the endosomal membrane by pore formation, partial solubilization or even disruption. The EDA might act, for example, by direct insertion into the endosomal membrane or indirectly by either affecting molecules that are critical for the maintenance of the integrity of the endosomal membrane or by inducing osmotic rupture ("proton sponge effect"). In one embodiment, the endosome destabilizing activity of the EDA is triggered by an external stimulus. The term "external stimulus", as used herein, refers to a stimulus to which the aqueous formulation and/or particles are exposed. It may, for example, be a change of the intracellular environment (e.g., a change of the pH value) or a stimulus selected from the group consisting of electromagnetic waves, such as light, and sound waves, such as ultrasound. In one embodiment, the EDA is a pH-reactive agent, e.g., selected from the group consisting of polymers and peptides, preferably amphipathic polymers and peptides. Such polymers and peptides may, for example, change their structural conformation upon exposure to a particular pH or pH range, e.g., from random coil at pH 7 to helical at a pH between 4.5 and 5.5. Suitable pH-reactive agents are know to a person skilled in the art. In another embodiment, the EDA is a photosensitizer, wherein, preferably, the endosome destabilizing activity of the photosensitizer is triggered by exposure to light. Suitable photosensitizers are know to a person skilled in the art.

The term "polycation", as used herein, refers to molecules or chemical complexes having positive charges at several sites, e.g. polycationic polymers, such as polyethylenimine and poly(amidoamine)s, and polycationic peptides/proteins, including cationic homo-polypeptides, such as poly-lysine and poly-arginine. The polycation preferably functions as a (poly)cationic carrier agent in the particles described herein.

The term "peptide", as used herein, comprises naturally or non-naturally occurring oligo- and polypeptides and refers to substances comprising two or more, preferably 3 or more, preferably 4 or more, preferably 6 or more, preferably 8 or more, preferably 10 or more, preferably 13 or more, preferably 16 more, preferably 21 or more and up to preferably 8, 10, 20, 30, 40 or 50, in particular 100 amino acids (e.g., 10 to 100, 10 to 50, 10 to 40, 20 to 100, 20 to 50 or 20 to 40 amino acids) joined covalently by peptide bonds. The term "protein" preferentially refers to large peptides, preferably to peptides with more than 100 amino acid residues, but in general the terms "peptide" and "protein" are synonyms and are used interchangeably herein.

A preferred polycation is protamine. The term "protamine" refers to strongly basic nuclear proteins ("protamines") of relatively low molecular weight that are rich in arginine and are found associated especially with DNA in place of somatic histones in the sperm cells of various animals (such as fish). In particular, the term "protamine" refers to proteins found in fish sperm that are strongly basic, are soluble in water, are not coagulated by heat, and yield chiefly arginine upon hydrolysis. Protamines have been used in a long-acting formulation of insulin and to neutralize the anticoagulant effects of heparin.

The term "protamine", as used herein, is meant to comprise any protamine amino acid sequence obtained or derived from native or biological sources including fragments thereof and multimeric forms of said amino acid sequence or fragments thereof. Furthermore, the term encompasses (synthesized) polypeptides which are artificial and specifically designed for specific purposes and cannot be isolated from native or biological sources. The protamine used according to the present invention can be sulfated protamine or hydrochloride protamine. In a preferred embodiment, the protamine source used for the production of the particles contains 1000 ("protamine 1000") to 5000 ("protamine 5000") heparin-neutralizing units per ml. Particularly preferred is protamine 5000. Isotonic protamine 1000 and 5000 stock solutions are, for example, commercially available from Meda Pharma under the trademarks Protamin® IPEX 1000 and 5000, respectively.

In the context of the present invention, the term "RNA" relates to a molecule which comprises ribonucleotide residues and preferably is entirely or substantially composed of ribonucleotide residues. "Ribonucleotide" relates to a nucleotide with a hydroxyl group at the 2'-position of a β-D-ribofuranosyl group. The term "RNA" comprises isolated RNA such as partially or completely purified RNA, essentially pure RNA, synthetic RNA, and recombinantly generated RNA and includes modified RNA which differs from naturally occurring RNA by addition, deletion, substitution and/or alteration of one or more nucleotides. Such alterations can include addition of non-nucleotide material, such as to the end(s) of a RNA or internally, for example at one or more nucleotides of the RNA. Nucleotides in RNA molecules can also comprise non-standard nucleotides, such as non-naturally occurring nucleotides or chemically synthesized nucleotides or deoxynucleotides. These altered RNAs can be referred to as analogs or analogs of naturally-occurring RNA.

According to the invention, "RNA" refers to single-stranded RNA or double stranded RNA and includes messenger RNA (mRNA), transfer RNA (tRNA), ribosomic RNA (rRNA), small nuclear RNA (snRNA), small inhibitory RNA (siRNA), small hairpin RNA (shRNA), microRNA (miRNA), antisense RNA, immunostimulating RNA (isRNA) and RNA aptamers. In a preferred embodiment, the RNA is selected from the group consisting of mRNA, siRNA, shRNA, miRNA, antisense RNA, isRNA and RNA aptamers.

The RNA may contain self-complementary sequences that allow parts of the RNA to fold and pair with itself to form double helices. According to the invention preferred as RNA are synthetic oligonucleotides of 6 to 100, preferably 10 to 50, in particular 15 to 30 or 15 to 20 nucleotides or messenger RNA (mRNA) of more than 50 nucleotides, preferably of 50 to 10,000, preferably 100 to 5000, in particular 200 to 3000 nucleotides.

According to the present invention, the term "messenger RNA (mRNA)" relates to a "transcript" which may be generated by using a DNA template and may encode a peptide or protein. Typically, an mRNA comprises a 5'-untranslated region, a protein coding region, and a 3'-untranslated region. In the context of the present invention, mRNA may be generated by in vitro transcription from a DNA template. The in vitro transcription methodology is known to the skilled person. For example, there is a variety of in vitro transcription kits commercially available.

According to the present invention, the term "small inhibitory RNA (siRNA)" relates to double stranded short (typically 19-23, preferably 21 nucleotides in length) oligonucleotides that can be used to induce the destruction of a target mRNA through the recognition of the target by one strand of the siRNA, a mechanism referred to as RNA interference (RNAi).

The term "small hairpin RNA (shRNA)" relates to a sequence of RNA that makes a tight hairpin turn and can be used to silence target gene expression via RNAi.

The terms "microRNA" or "miRNA" relate to a small non-coding RNA molecule (typically 19-25 nucleotides in length), which functions in transcriptional and post-transcriptional regulation of gene expression.

According to the present invention, the term "antisense RNA" relates to a single stranded RNA, usually a synthetic oligonucleotide that is designed to base-pair with a targeted cellular mRNA, thereby inhibiting physically the process of translation and eventually inducing destruction of the targeted mRNA.

According to the present invention, "immunostimulating RNA (isRNA)" relates to RNA that can activate innate immune receptors, such as, for example, the endoplasmic TLR-3, 7 and 8 or the cytosolic protein RIG-1. In one embodiment, the isRNA comprises one or more uridine (U) nucleotides.

According to the present invention, the term "RNA aptamer" relates to RNA that through its precise three dimensional structure can be used as an antibody, i.e., made to bind specifically to determined structures and thereby activate or block biological mechanisms.

According to the invention, the RNA may be modified. For example, RNA may be stabilized by one or more modifications having stabilizing effects on RNA.

The term "modification" in the context of RNA as used according to the present invention includes any modification of RNA which is not naturally present in said RNA.

In one embodiment of the invention, the RNA used according to the invention does not have uncapped 5'-triphosphates. Removal of such uncapped 5'-triphosphates can be achieved by treating RNA with a phosphatase.

The RNA according to the invention may have modified naturally occurring or non-naturally occurring (synthetic) ribonucleotides in order to increase its stability and/or decrease cytotoxicity and/or modulate its immunostimulating potential. For example, in one embodiment, in the RNA used according to the invention uridine is substituted partially or completely, preferably completely, by pseudouridine.

In one embodiment, the term "modification" relates to providing a RNA with a 5'-cap or 5'-cap analog. The term "5'-cap" refers to a cap structure found on the 5'-end of an mRNA molecule and generally consists of a guanosine nucleotide connected to the mRNA via an unusual 5' to 5' triphosphate linkage. In one embodiment, this guanosine is methylated at the 7-position. The term "conventional 5'-cap" refers to a naturally occurring RNA 5'-cap, preferably to the 7-methylguanosine cap ($m^7G$). In the context of the present invention, the term "5'-cap" includes a 5'-cap analog that resembles the RNA cap structure and is modified to possess the ability to stabilize RNA if attached thereto, preferably in vivo and/or in a cell. Providing an RNA with a 5'-cap or 5'-cap analog may be achieved by in vitro transcription of a DNA template in the presence of said 5'-cap or 5'-cap analog, wherein said 5'-cap is co-transcriptionally incorporated into the generated RNA strand, or the RNA may be generated, for example, by in vitro transcription, and the 5'-cap may be generated post-transcriptionally using capping enzymes, for example, capping enzymes of vaccinia virus.

The RNA may comprise further modifications. For example, a modification of mRNA used in the present invention may be an extension or truncation of the naturally occurring poly(A) tail.

The term "stability" of RNA relates to the "half-life" of RNA. "Half-life" relates to the period of time which is needed to eliminate half of the activity, amount, or number of molecules. In the context of the present invention, the half-life of a RNA is indicative for the stability of said RNA.

If, according to the present invention, it is desired to decrease stability of RNA, it is also possible to modify RNA so as to interfere with the function of elements as described above increasing the stability of RNA.

According to the present invention, RNA may be obtained by chemical synthesis or by in vitro transcription of an appropriate DNA template. In the context of the present invention, the term "transcription" relates to a process, wherein the genetic code in a DNA sequence is transcribed into RNA. Subsequently, the RNA may be translated into protein. According to the present invention, the term "transcription" comprises "in vitro transcription", wherein the term "in vitro transcription" relates to a process wherein RNA, in particular mRNA, is in vitro synthesized in a cell-free system, preferably using appropriate cell extracts. Preferably, cloning vectors are applied for the generation of transcripts. These cloning vectors are generally designated as transcription vectors and are according to the present invention encompassed by the term "vector". The promoter for controlling transcription can be any promoter for any RNA polymerase. Particular examples of RNA polymerases are the T7, T3, and SP6 RNA polymerases. A DNA template for in vitro transcription may be obtained by cloning of a nucleic acid, in particular cDNA, and introducing it into an appropriate vector for in vitro transcription.

The cDNA may be obtained by reverse transcription of RNA. Preferably, cloning vectors are used for producing transcripts which generally are designated transcription vectors.

The term "translation" according to the invention relates to the process in the ribosomes of a cell by which a strand of messenger RNA directs the assembly of a sequence of amino acids to make a peptide or protein.

The term "inhibition of gene expression" relates to a process, wherein RNA oligonucleotides (e.g., single stranded antisense or double stranded siRNA) can be used to bind specific mRNA sequences inducing either the degradation of the targeted mRNA and/or to the blockade of translation.

According to the present invention, the polycation:RNA mass ratio is preferably 1:2 or higher (e.g., 1:1, 2:1 or 4:1). In one embodiment, the particles have a polycation:RNA mass ratio in the range of from 16:1 to 1:2, preferably in the range of from 8:1 to 1:2, more preferably in the range of from 4:1 to 1:2. In a particularly preferred embodiment, the particles have a polycation:RNA mass ratio in the range of from 4:1 to 1:1. In one embodiment, the particles of the invention have a polycation:RNA mass ratio of 2:1.

The term "non-electrolyte osmotic agent", as used herein, refers to a chemical substance or composition which provides an osmotic effect in an aqueous solution and which is not an electrolyte or salt. Preferably, the non-electrolyte osmotic agent is pharmaceutically acceptable.

In one embodiment, the non-electrolyte osmotic agent is a sugar, wherein, preferably, the sugar is selected from monosaccharides, disaccharides and oligosaccharides, more preferably monosaccharides. In one embodiment, the sugar is selected from the group consisting of glucose, fructose and mannose. The terms "glucose", "fructose" and "mannose", as used herein, include both the D-form and L-form of these sugars, wherein the D-form is preferred. In one embodiment, the sugar is glucose.

In the context of the present invention the terms "salt(s)" and "electrolyte(s)" are used interchangeably and mean a compound that at least partially dissociates into its respective counter ions in water.

According to the present invention, the term "mM electrolytes" means the concentration in $10^{-3}$ mol per liter of the sum of all electrolytes (including inorganic salts such as NaCl, $CaCl_2$, KCl, $NaH_2PO_4$, $Na_2HPO_4$, $KH_2PO_4$, $K_2HPO_4$, $MgCl_2$, $MnCl_2$, $Na_2SO_4$, $K_2SO_4$, $MgSO_4$ and salts such Tris-HCl, EDTA, Hepes, etc.), e.g., in the aqueous formulation according to the present invention.

The aqueous formulation according to the present invention or prepared according to the present invention comprises less than 50 mM electrolytes, preferably less than 25 mM electrolytes, more preferably less than 15 mM electrolytes, even more preferably less than 10 mM electrolytes, even more preferably less than 5 mM electrolytes, even more preferably less than 2.5 mM electrolytes.

In one embodiment, the aqueous formulation is a low-salt aqueous formulation which comprises between 0.5 mM and 50 mM electrolyte(s), preferably between 0.5 mM and 25 mM electrolyte(s), more preferably between 0.5 mM and 15 mM electrolyte(s), even more preferably between 0.5 mM and 10 mM electrolyte(s), even more preferably between 0.5 mM and 5 mM electrolyte(s), even more preferably between 0.5 mM and 2.5 mM electrolyte(s), e.g., approximately 1.5 mM electrolyte(s). In one embodiment, the electrolyte(s) comprise(s) calcium. In a preferred embodiment, the electrolyte is $CaCl_2$. In one embodiment, the electrolyte(s) allow or enhance a biological activity of the particles and/or of any other component included in the aqueous formulation (e.g., an additional therapeutic agent as described herein, such as a free, i.e. non-particle bound, mRNA molecule).

In one embodiment, the aqueous formulation does not comprise any electrolytes or salts.

The term "isotonic" refers to the tonicity of a solution/formulation which can be used to in vitro manipulate cells without causing hypotonic or hypertonic shock, i.e. the cells neither shrink nor swell upon exposure to the solution/formulation. The osmolarity of such solutions/formulations is similar to the one of blood serum, i.e. it is in the range of from 295 to 315 mOsm/L, more particularly in the range of from 300 to 310 mOsm/L. Formulations or compositions to be administered through parenteral routes are usually isotonic so that they do not damage cells in vivo upon administration.

The aqueous formulations and pharmaceutical compositions described herein may be administered via any conventional route, such as by parenteral administration including by injection or infusion. Administration is preferably parenterally, e.g., intravenously, intraarterially, subcutaneously, in the lymph node, intradermally or intramuscularly.

The aqueous formulations and pharmaceutical compositions described herein are administered in effective amounts and/or contain an effective amount of particles comprising a polycation, preferably protamine, and RNA. An "effective amount" refers to the amount which achieves a desired reaction or a desired effect alone or together with further doses. In the case of treatment of a particular disease or of a particular condition, the desired reaction preferably relates to inhibition of the course of the disease. This comprises slowing down the progress of the disease and, in particular, interrupting or reversing the progress of the disease. The desired reaction in a treatment of a disease or of a condition may also be delay of the onset or a prevention of the onset of said disease or said condition.

An effective amount of an aqueous formulation or pharmaceutical composition described herein or of the particles comprised by them will depend on the condition to be treated, the severeness of the disease, the individual parameters of the patient, including age, physiological condition, size and weight, the duration of treatment, the type of an accompanying therapy (if present), the specific route of administration and similar factors. Accordingly, the doses administered of the agents described herein may depend on several of these parameters. In the case that a reaction in a patient is insufficient with an initial dose, higher doses (or effectively higher doses achieved by a different, more localized route of administration) may be used.

An aqueous formulation or pharmaceutical composition according to the present invention is preferably sterile and may further comprise one or more excipients, all of which are preferably pharmaceutically acceptable.

The term "pharmaceutically acceptable", as used herein, refers to the non-toxicity of a material which does not interfere with the action of the active component(s) of the aqueous formulation or pharmaceutical composition.

The term "excipient", as used herein, is intended to include all substances which may be present in a pharmaceutical composition of the present invention and which are not active ingredients such as, e.g., carriers, binders, lubricants, thickeners, surface active agents, preservatives, emulsifiers, buffers, flavoring agents, or colorants.

The aqueous formulation or pharmaceutical composition may also comprise further agents as discussed herein, such as an EDA and an additional therapeutic agent (e.g., an antigen). An aqueous formulation or pharmaceutical composition according to the present invention may also comprise an additional immunomodulating agent, such as anti-CTL-A4, or anti-regulatory T-cell reagents, such as an anti-CD25 antibody or cyclophosphamide or an adjuvant.

The term "adjuvant" relates to compounds which prolong or enhance or accelerate an immune response. Particularly preferred adjuvants are cytokines, such as monokines, lymphokines, interleukines or chemokines, e.g. IL-1, IL-2, IL-3, IL-4, IL-5, IL-6, IL-7, IL-8, IL-9, IL-10, IL-12, INFα, INF-γ, GM-CSF, LT-α, or growth factors, e.g. hGH. Further known adjuvants are aluminium hydroxide, Freund's adjuvant or oil such as Montanide®, e.g., Montanide® ISA51. Lipopeptides, such as Pam3Cys, are also suitable for use as adjuvants in the aqueous formulation or pharmaceutical composition of the present invention.

Pharmaceutical compositions are usually provided in a uniform dosage form and may be prepared in a manner known in the art. The pharmaceutical composition of the invention may, e.g., be in the form of a solution, suspension or emulsion. In one embodiment, the pharmaceutical composition is formulated as an emulsion containing an oil, such a Montanide®.

As used herein, the term "kit" refers to an article of manufacture comprising one or more containers and, optionally, a data carrier. Said one or more containers may be filled with one or more of the above mentioned means or reagents, e.g. an aqueous formulation as defined above. Additional containers may be included in the kit that contain, e.g., diluents, buffers and further reagents. Said data carrier may be a non-electronic data carrier, e.g., a graphical data carrier such as an information leaflet, an information sheet, a bar code or an access code, or an electronic data carrier such as a floppy disk, a compact disk (CD), a digital versatile disk (DVD), a microchip or another semiconductor-based electronic data carrier. The access code may allow the access to a database, e.g., an internet database, a centralized, or a decentralized database. Said data carrier may comprise instructions for the use of the kit in accordance with the present invention.

The present invention also relates to aqueous formulations as defined herein or pharmaceutical compositions or kits as defined herein for use in a method of treatment or prevention of a disease or for use in a method of immunostimulation. The present invention further relates to aqueous formulations as defined herein or kits as defined herein for use in a method of transfection, in particular transfection of cells with RNA.

The present invention also relates to the use of an aqueous formulation as defined herein or of a pharmaceutical composition as defined herein in the manufacture of a medicament for the treatment or prevention of a disease or for use in a method of immunostimulation.

The present invention further relates to a method of treatment or prevention of a disease or to a method of immunostimulation, the methods comprising the step of administering an aqueous formulation as defined herein or a pharmaceutical composition as defined herein to a subject in need thereof.

The particles comprised by the aqueous formulations, pharmaceutical compositions and kits lead to the efficient release of RNA in the cytosol, allowing biological activities of RNA such as protein expression, interference with gene expression, or immunostimulation. Therefore, the aqueous formulations, pharmaceutical compositions and kits of the present invention are useful to interfere with gene expression (e.g. by delivering antisense RNA or siRNA), modify protein activities (e.g. by delivering RNA aptamers), complement a deficient gene (e.g. by delivering non-immunostimulating mRNA) or activate immunity (e.g. by delivering isRNA or mRNA vaccines) in certain disease states, in particular in the case of chronic diseases, such as cancer, infectious diseases, allergies and autoimmune diseases. Thus, the aqueous formulations, pharmaceutical compositions and kits of the present invention are particularly useful in the treatment of said diseases.

According to the present invention, the RNA can be coding RNA (e.g. mRNA), i.e. RNA encoding a peptide or protein, such as a pharmaceutically active peptide or protein. Said RNA may express the encoded peptide or protein. For example, said RNA may be RNA encoding and expressing an antigen, or a pharmaceutically active peptide or protein such as an immunologically active compound (which preferably is not an antigen). Alternatively, the RNA can be non-coding RNA such as antisense-RNA, micro RNA (miRNA) or siRNA.

According to the invention, the term "RNA encoding a peptide or protein" means that the RNA, if present in the appropriate environment, preferably within a cell, can direct the assembly of amino acids to produce the peptide or protein during the process of translation. Preferably, RNA according to the invention is able to interact with the cellular translation machinery allowing translation of the peptide or protein.

According to the invention, RNA comprises or consists of pharmaceutically active RNA. A "pharmaceutically active RNA" is a RNA that encodes a pharmaceutically active peptide or protein or is pharmaceutically active on its own, e.g., it has one or more pharmaceutical activities such as those described for pharmaceutically active proteins. For example, the RNA may be one or more strands of RNA interference (RNAi). Such agents include short interfering RNAs (siRNAs), or short hairpin RNAs (shRNAs), or precursor of a siRNA or microRNA-like RNA, targeted to a target transcript, e.g., a transcript of an endogenous disease-related transcript of a subject.

A "pharmaceutically active peptide or protein" has a positive or advantageous effect on the condition or disease state of a subject when administered to the subject in a therapeutically effective amount. Preferably, a pharmaceutically active peptide or protein has curative or palliative properties and may be administered to ameliorate, relieve, alleviate, reverse, delay onset of or lessen the severity of one or more symptoms of a disease or disorder. A pharmaceutically active peptide or protein may have prophylactic properties and may be used to delay the onset of a disease or to lessen the severity of such disease or pathological condition. The term "pharmaceutically active peptide or protein" includes entire proteins or polypeptides, and can also refer to pharmaceutically active fragments thereof. It can also include pharmaceutically active analogs of a peptide or protein. The term "pharmaceutically active peptide or protein" includes peptides and proteins that are antigens, i.e., administration of the peptide or protein to a subject elicits an immune response in a subject which may be therapeutic or partially or fully protective.

Examples of pharmaceutically active proteins include, but are not limited to, cytokines and immune system proteins such as immunologically active compounds (e.g., interleukins, colony stimulating factor (CSF), granulocyte colony stimulating factor (G-CSF), granulocyte-macrophage colony stimulating factor (GM-CSF), erythropoietin, tumor necrosis factor (TNF), interferons, integrins, addressins, seletins, homing receptors, T cell receptors, immunoglobulins, soluble major histocompatibility complex antigens, immunologically active antigens such as bacterial, parasitic, or viral antigens, allergens, autoantigens, antibodies), hormones (insulin, thyroid hormone, catecholamines, gonadotrophines, trophic hormones, prolactin, oxytocin, dopamine, bovine somatotropin, leptins and the like), growth hormones (e.g., human grown hormone), growth factors (e.g., epidermal growth factor, nerve growth factor, insulin-like growth factor and the like), growth factor receptors, enzymes (tissue plasminogen activator, streptokinase, cholesterol biosynthetic or degradative, steriodogenic enzymes, kinases, phosphodiesterases, methylases, de-methylases, dehydrogenases, cellulases, proteases, lipases, phospholipases, aromatases, cytochromes, adenylate or guanylaste cyclases, neuramidases and the like), receptors (steroid hormone receptors, peptide receptors), binding proteins (growth hormone or growth factor binding proteins and the like), transcription and translation factors, tumor growth suppressing proteins (e.g., proteins which inhibit angiogenesis), structural proteins (such as collagen, fibroin, fibrinogen, elastin, tubulin, actin, and myosin), blood proteins (thrombin, serum albumin, Factor VII, Factor VIII, insulin, Factor IX, Factor X, tissue plasminogen activator, protein C, von Wilebrand factor, antithrombin III, glucocerebrosidase, erythropoietin granulocyte colony stimulating factor (GCSF) or modified Factor VIII, anticoagulants and the like.

In one embodiment, the pharmaceutically active protein according to the invention is a cytokine which is involved in regulating lymphoid homeostasis, preferably a cytokine which is involved in and preferably induces or enhances development, priming, expansion, differentiation and/or survival of T cells. In one embodiment, the cytokine is an interleukin. In one embodiment, the pharmaceutically active protein according to the invention is an interleukin selected from the group consisting of IL-2, IL-7, IL-12, IL-15, and IL-21.

The term "immunologically active compound" relates to any compound altering an immune response, preferably by inducing and/or suppressing maturation of immune cells, inducing and/or suppressing cytokine biosynthesis, and/or altering humoral immunity by stimulating antibody production by B cells. Immunologically active compounds possess potent immunostimulating activity including, but not limited to, antiviral and antitumor activity, and can also downregulate other aspects of the immune response, for example shifting the immune response away from a TH2 immune response, which is useful for treating a wide range of TH2 mediated diseases. Immunologically active compounds can be useful as vaccine adjuvants. In one embodiment, the RNA forming a hydrophilic shell on at least a portion of the vesicular core of the particles described herein encodes an immunologically active compound. Said compound preferably does not encode an antigen.

If, according to the present invention, it is desired to induce or enhance an immune response by using aqueous formulations or pharmaceutical compositions as described herein, the immune response may be triggered or enhanced by the RNA. For example, proteins or peptides encoded by the RNAs or procession products thereof may be presented by major histocompatibility complex (MHC) proteins expressed on antigen presenting cells. The MHC peptide complex can then be recognized by immune cells such as T cells leading to their activation.

The term "disease" refers to an abnormal condition that affects the body of an individual. A disease is often construed as a medical condition associated with specific symptoms and signs. A disease may be caused by factors originally from an external source, such as infectious disease, or it may be caused by internal dysfunctions, such as autoimmune diseases.

According to the invention, the term "disease" also refers to cancer diseases. The terms "cancer disease" or "cancer" (medical term: malignant neoplasm) refer to a class of diseases in which a group of cells display uncontrolled growth (division beyond the normal limits), invasion (intrusion on and destruction of adjacent tissues), and sometimes metastasis (spread to other locations in the body via lymph or blood). These three malignant properties of cancers differentiate them from benign tumors, which are self-limited, and do not invade or metastasize. Most cancers form a tumor, i.e. a swelling or lesion formed by an abnormal growth of cells (called neoplastic cells or tumor cells), but some, like leukemia, do not. Examples of cancers include, but are not limited to, carcinoma, lymphoma, blastoma, sarcoma, glioma and leukemia. More particularly, examples of such cancers include bone cancer, blood cancer, lung cancer, liver cancer, pancreatic cancer, skin cancer, cancer of the head or neck, cutaneous or intraocular malignant melanoma, uterine cancer, ovarian cancer, rectal cancer, cancer of the anal region, stomach cancer, colon cancer, breast cancer, prostate cancer, uterine cancer, carcinoma of the sexual and reproductive organs, Hodgkin's disease, cancer of the esophagus, cancer of the small intestine, cancer of the endocrine system, cancer of the thyroid gland, cancer of the parathyroid gland, cancer of the adrenal gland, sarcoma of soft tissue, cancer of the bladder, cancer of the kidney, renal cell carcinoma, carcinoma of the renal pelvis, neoplasms of the central nervous system (CNS), neuroectodermal cancer, spinal axis tumors, glioma, meningioma, and pituitary adenoma. The term "cancer" according to the invention also comprises cancer metastases.

Malignant melanoma is a serious type of skin cancer. It is due to uncontrolled growth of pigment cells, called melanocytes.

According to the invention, a "carcinoma" is a malignant tumor derived from epithelial cells. This group represents the most common cancers, including the common forms of breast, prostate, lung and colon cancer.

Lymphoma and leukemia are malignancies derived from hematopoietic (blood-forming) cells.

A sarcoma is a cancer that arises from transformed cells in one of a number of tissues that develop from embryonic mesoderm. Thus, sarcomas include tumors of bone, cartilage, fat, muscle, vascular, and hematopoietic tissues.

Blastic tumor or blastoma is a tumor (usually malignant) which resembles an immature or embryonic tissue. Many of these tumors are most common in children.

A glioma is a type of tumor that starts in the brain or spine. It is called a glioma because it arises from glial cells. The most common site of gliomas is the brain.

By "metastasis" is meant the spread of cancer cells from its original site to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor, i.e. a secondary tumor or metastatic tumor, at the target site depends on angiogenesis. Tumor metastasis often occurs even after the removal of the primary tumor because tumor cells or components may remain and develop metastatic potential. In one embodiment, the term "metastasis" according to the invention relates to "distant metastasis" which relates to a metastasis which is remote from the primary tumor and the regional lymph node system.

The term "infectious disease" refers to any disease which can be transmitted from individual to individual or from organism to organism, and is caused by a microbial agent (e.g. common cold). Examples of infectious diseases treatable with the aqueous formulations and pharmaceutical compositions of the present invention include viral infectious diseases, such as AIDS (HIV), hepatitis A, B or C, herpes, herpes zoster (chicken-pox), German measles (rubella virus), yellow fever, dengue etc. flaviviruses, influenza viruses, hemorrhagic infectious diseases (Marburg or Ebola viruses), and severe acute respiratory syndrome (SARS), bacterial infectious diseases, such as Legionnaire's disease (*Legionella*), sexually transmitted diseases (e.g. chlamydia or gonorrhea), gastric ulcer (*Helicobacter*), cholera (*Vibrio*), tuberculosis, diphtheria, infections by *E. coli*, Staphylococci, *Salmonella* or Streptococci (tetanus); infections by protozoan pathogens such as malaria, sleeping sickness, leishmaniasis; toxoplasmosis, i.e. infections by *Plasmodium, Trypanosoma, Leishmania* and *Toxoplasma*; or fungal infections, which are caused e.g. by *Cryptococcus neoformans, Histoplasma capsulatum, Coccidioides immitis, Blastomyces dermatitidis* or *Candida albicans*.

The aqueous formulations, pharmaceutical compositions and kits of the present invention are also useful in treating allergies and autoimmune diseases. The term "autoimmune disease" refers to any disease in which the body produces an immunogenic (i.e. immune system) response to some constituent of its own tissue. In other words, the immune system loses its ability to recognize some tissue or system within the body as self and targets and attacks it as if it were foreign. Autoimmune diseases can be classified into those in which predominantly one organ is affected (e.g. hemolytic anemia and anti-immune thyroiditis), and those in which the autoimmune disease process is diffused through many tissues (e.g. systemic lupus erythematosus). For example, multiple sclerosis is thought to be caused by T cells attacking the sheaths that surround the nerve fibers of the brain and spinal cord. This results in loss of coordination, weakness, and blurred vision. Autoimmune diseases are known in the art and include, for instance, Hashimoto's thyroiditis, Grave's disease, lupus, multiple sclerosis, rheumatic arthritis, hemolytic anemia, anti-immune thyroiditis, systemic lupus erythematosus, celiac disease, Crohn's disease, colitis, diabetes, scleroderma, psoriasis, and the like.

The aqueous formulations, pharmaceutical compositions and kits of the present invention can also be utilized to deliver RNA that may correct an inherited genetic disease such as cystic fibrosis or myopathies (e.g., by facilitating or blocking a particular biological activity). Similarly, they can be used to achieve production of therapeutic proteins (for example enzymes or recombinant antibodies) by the own cells of the treated patients.

The aqueous formulations and pharmaceutical compositions of the present invention can also be used in conjunction with another therapeutic agent which can be administered prior to, simultaneously with or after administration of the aqueous formulations or pharmaceutical compositions of the present invention. Such therapeutic agents include immunomodulating agents, which may be immunostimulating or immunosuppressive, chemotherapeutic drugs for cancer patients, e.g. gemcitabine, etopophos, cis-platin, carbo-platin, antiviral agents, anti-parasite agents or an anti-bacterial agents and, if administered simultaneously with the aqueous formulations of the present invention, may be present in a pharmaceutical composition of the present invention.

The aqueous formulations and pharmaceutical compositions of the present invention may also be used in genetic vaccination, wherein an immune response is stimulated by introducing into a subject a suitable mRNA which codes for an antigen or a fragment thereof, e.g., a disease-associated antigen.

The term "antigen" relates to an agent comprising an epitope against which an immune response is to be generated. The term "antigen" includes in particular proteins, peptides, polysaccharides, nucleic acids, especially RNA and DNA, and nucleotides. The term "antigen" also includes agents, which become antigenic—and sensitizing—only through transformation (e.g. intermediately in the molecule or by completion with body protein). An antigen is preferably presentable by cells of the immune system such as antigen presenting cells like dendritic cells or macrophages. In addition, an antigen or a processing product thereof is preferably recognizable by a T or B cell receptor, or by an immunoglobulin molecule such as an antibody. In a preferred embodiment, the antigen is a disease-associated antigen, such as a tumor-associated antigen, a viral antigen, or a bacterial antigen.

The term "disease-associated antigen" is used in its broadest sense to refer to any antigen associated with a disease. A disease-associated antigen is a molecule which contains epitopes that will stimulate a host's immune system to make a cellular antigen-specific immune response and/or a humoral antibody response against the disease. The disease-associated antigen may therefore be used for therapeutic purposes. Disease-associated antigens are preferably associated with infection by microbes, typically microbial antigens, or associated with cancer, typically tumors.

The term "disease involving an antigen" refers to any disease which implicates an antigen, e.g. a disease which is characterized by the presence of an antigen. The disease involving an antigen can be an infectious disease, an autoimmune disease, or a cancer disease or simply cancer. As mentioned above, the antigen may be a disease-associated antigen, such as a tumor-associated antigen, a viral antigen, or a bacterial antigen.

In one embodiment, a disease-associated antigen is a tumor-associated antigen. In this embodiment, the aqueous formulations and pharmaceutical compositions of the present invention may be useful in treating cancer or cancer metastasis. Preferably, the diseased organ or tissue is characterized by diseased cells such as cancer cells expressing a disease-associated antigen and/or being characterized by association of a disease-associated antigen with their surface. Immunization with intact or substantially intact tumor-associated antigens or fragments thereof such as MHC class I and class II peptides or nucleic acids, in particular mRNA, encoding such antigen or fragment makes it possible to elicit a MHC class I and/or a class II type response and, thus, stimulate T cells such as CD8+ cytotoxic T lymphocytes which are capable of lysing cancer cells and/or CD4+ T cells. Such immunization may also elicit a humoral immune response (B cell response) resulting in the production of antibodies against the tumor-associated antigen. Furthermore, antigen presenting cells (APC) such as dendritic cells (DCs) can be loaded with MHC class I—presented peptides by transfection with nucleic acids encoding tumor antigens in vitro and administered to a patient. In one embodiment, the term "tumor-associated antigen" refers to a constituent of cancer cells which may be derived from the cytoplasm, the cell surface and the cell nucleus. In particular, it refers to those antigens which are produced, preferably in large quantity, intracellularly or as surface antigens on tumor cells. Examples for tumor antigens include HER2, EGFR, VEGF, CAMPATH1-antigen, CD22, CA-125, HLA-DR, Hodgkin-lymphoma or mucin-1, but are not limited thereto.

According to the present invention, a tumor-associated antigen preferably comprises any antigen which is characteristic for tumors or cancers as well as for tumor or cancer cells with respect to type and/or expression level. In one embodiment, the term "tumor-associated antigen" relates to proteins that are under normal conditions, i.e. in a healthy subject, specifically expressed in a limited number of organs and/or tissues or in specific developmental stages, for example, the tumor-associated antigen may be under normal conditions specifically expressed in stomach tissue, preferably in the gastric mucosa, in reproductive organs, e.g., in testis, in trophoblastic tissue, e.g., in placenta, or in germ line cells, and are expressed or aberrantly expressed in one or more tumor or cancer tissues. In this context, "a limited number" preferably means not more than 3, more preferably not more than 2 or 1. The tumor-associated antigens in the context of the present invention include, for example, differentiation antigens, preferably cell type specific differentiation antigens, i.e., proteins that are under normal conditions specifically expressed in a certain cell type at a certain differentiation stage, cancer/testis antigens, i.e., proteins that are under normal conditions specifically expressed in testis and sometimes in placenta, and germ line specific antigens. In the context of the present invention, the tumor-associated antigen is preferably not or only rarely expressed in normal tissues or is mutated in tumor cells. Preferably, the tumor-associated antigen or the aberrant expression of the tumor-associated antigen identifies cancer cells. In the context of the present invention, the tumor-associated antigen that is expressed by a cancer cell in a subject, e.g., a patient suffering from a cancer disease, is preferably a self-protein in said subject. In preferred embodiments, the tumor-associated antigen in the context of the present invention is expressed under normal conditions specifically in a tissue or organ that is non-essential, i.e., tissues or organs which when damaged by the immune system do not lead to death of the subject, or in organs or structures of the body which are not or only hardly accessible by the immune system. Preferably, a tumor-associated antigen is presented in the context of MHC molecules by a cancer cell in which it is expressed.

Examples for differentiation antigens which ideally fulfill the criteria for tumor-associated antigens as contemplated by the present invention as target structures in tumor immunotherapy, in particular, in tumor vaccination are the cell surface proteins of the Claudin family, such as CLDN6 and CLDN18.2. These differentiation antigens are expressed in tumors of various origins, and are particularly suited as target structures in connection with antibody-mediated cancer immunotherapy due to their selective expression (no expression in a toxicity relevant normal tissue) and localization to the plasma membrane.

Further examples for antigens that may be useful in the present invention are p53, ART-4, BAGE, beta-catenin/m, Bcr-abL CAMEL, CAP-1, CASP-8, CDC27/m, CDK4/m, CEA, CLAUDIN-12, c-MYC, CT, Cyp-B, DAM, ELF2M, ETV6-AML1, G250, GAGE, GnT-V, Gap100, HAGE, HER-2/neu, HPV-E7, HPV-E6, HAST-2, hTERT (or hTRT), LAGE, LDLR/FUT, MAGE-A, preferably MAGE-A1, MAGE-A2, MAGE-A3, MAGE-A4, MAGE-A5, MAGE-A6, MAGE-A7, MAGE-A8, MAGE-A9, MAGE-A10, MAGE-A11, or MAGE-A12, MAGE-B, MAGE-C, MART-1/Melan-A, MC1R, Myosin/m, MUC1, MUM-1, -2, -3, NA88-A, NF1, NY-ESO-1, NY-BR-1, p190 minor BCR-abL, Pm1/RARa, PRAME, proteinase 3, PSA, PSM, RAGE, RU1 or RU2, SAGE, SART-1 or SART-3, SCGB3A2, SCP1, SCP2, SCP3, SSX, SURVIVIN, TEL/AML1, TPI/m, TRP-1, TRP-2, TRP-2/INT2, TPTE and WT, preferably WT-1.

The term "viral antigen" refers to any viral component having antigenic properties, i.e. being able to provoke an immune response in an individual. The viral antigen may be a viral ribonucleoprotein or an envelope protein.

The term "bacterial antigen" refers to any bacterial component having antigenic properties, i.e. being able to provoke an immune response in an individual. The bacterial antigen may be derived from the cell wall or cytoplasm membrane of the bacterium.

The term "immune response", as used herein, relates to a reaction of the immune system such as to immunogenic organisms, such as bacteria or viruses, cells or substances. The term "immune response" includes the innate immune response and the adaptive immune response. Preferably, the immune response is related to an activation of immune cells, an induction of cytokine biosynthesis and/or antibody production.

It is preferred that the immune response induced by the aqueous formulations or pharmaceutical compositions described herein comprises the steps of activation of antigen presenting cells, such as dendritic cells and/or macrophages, presentation of an antigen or fragment thereof by said antigen presenting cells and activation of cytotoxic T cells due to this presentation.

By "treat" it is meant to administer a formulation or composition as described herein to a subject in order eliminate a disease, including reducing the size of a tumor or the number of tumors in a subject; arrest or slow a disease in a subject; inhibit or slow the development of a new disease in a subject; decrease the frequency or severity of symptoms and/or recurrences in a subject who currently has or who previously has had a disease; and/or prolong, i.e. increase the lifespan of the subject.

In particular, the term "treatment of a disease" includes curing, shortening the duration, ameliorating, slowing down or inhibiting progression or worsening of a disease or the symptoms thereof.

The term "immunotherapy" relates to a treatment preferably involving a specific immune reaction and/or immune effector function(s).

The term "immunization" or "vaccination" describes the process of treating a subject for therapeutic or prophylactic reasons.

The term "subject", as used herein, preferably relates to mammals. For example, mammals in the context of the present invention are humans, non-human primates, domesticated animals such as dogs, cats, sheep, cattle, goats, pigs, horses etc., laboratory animals such as mice, rats, rabbits, guinea pigs, etc. as well as animals in captivity, such as animals of zoos. In a preferred embodiment, the subject is a human.

Aqueous formulations or pharmaceutical compositions of the invention when contacted with appropriate cells or administered to a subject are capable of leading to the production of the protein encoded by the mRNA or to the inhibition of expression of the gene(s) targeted by the siRNA/antisense RNA or to the release in the cytosol of RNA aptamers contained in the particles comprised by them.

Should they contain immunostimulating RNA (isRNA), aqueous formulations or pharmaceutical compositions of the invention when contacted with appropriate cells or administered to a subject are capable of inducing cytokines. Thus, the aqueous formulations or pharmaceutical compositions according to the invention are useful as a mRNA vaccine.

Should they contain non-immunostimulating RNA, aqueous formulations or pharmaceutical compositions of the invention when contacted with appropriate cells or administered to a subject do not induce cytokines. Thus, the aqueous formulations or pharmaceutical compositions according to the invention are useful for gene therapy (mRNA) or gene interference (antisense or siRNA) or protein inhibition (aptamer).

The present invention also relates to a method for simultaneously providing an antigen (encoded by an mRNA) and stimulating the innate immune system of a subject, the method comprising administering to the subject an effective amount of aqueous formulations or pharmaceutical compositions of the present invention. The stimulation of the innate immune system preferably involves the stimulation of one or more of TLR-7, TLR-8 and TLR-3. A concomitant stimulation of the adaptive immune system (specific B- and T-lymphocytes) is possible thanks to the expression of the mRNA-encoded antigen.

The present invention also provides an ex vivo method for functional delivery of RNA into cells by contacting the cells with aqueous formulations or pharmaceutical compositions of the present invention. These transfected cells can be transferred into a subject, such as the subject from whom the cells were obtained, to operate the therapeutic function. In one embodiment, suitable cells are isolated from a subject and treated in vitro by adding to the isolated cells an effective amount of aqueous formulations or pharmaceutical compositions of the present invention. Afterwards, the transfected cells are (re-)introduced into the subject. Suitable cells for such ex vivo treatment include but are not limited to stem cells (pluripotent cells), immune cells, such as dendritic cells, B-cells and natural killer (NK) cells.

"Physically stabilizing" particles comprising a polycation, preferably protamine, and RNA aims at maintaining the particles in their original physical state, wherein, preferably, physical stabilization is achieved without compromising the biological activity of the particles. In a preferred embodiment, "physically stabilizing" comprises reducing or preventing enlargement of the particles over time. In one embodiment, enlargement of the particles to a(n average) size of more than 450 nm is reduced or prevented.

The following examples are intended to illustrate preferred embodiments of the invention and should not be interpreted to limit the scope of the invention as defined in the claims.

EXAMPLES

Example 1: Method for the Preparation of a Stable and Isotonic Protamine-RNA Nanoparticle Formulation An RNA molecule was synthesized and purified. The product was then lyophilized and resuspended at 1 mg/ml in deionized water (herein also referred to as "pure water"). Protamin® IPEX 5000 was diluted 14-fold in pure water to provide a low-salt solution of protamine at approximately 1 mg/ml. One volume of RNA was mixed with two volumes of protamine. Immediate and intensive mixing was performed, for example, by pipetting up and down or by vortexing. The formulation was left for ten minutes at room temperature and then further diluted with an excess (at least 5 volumes) of 5% glucose. Alternatively, an equal volume of 10% glucose can be added in order to obtain protamine-RNA nanoparticles at a final glucose concentration of 5%. Under these conditions, as shown in FIG. 1, the size of the protamine-RNA particles was stable over time. On the contrary, when the particles are formulated in salty solutions such as PBS, they got larger over time.

Example 2: Immunostimulating Capacities of Protamine-RNA Nanoparticles are Preserved in 5% Sugar Formulations Three microliters of a mixture containing 0.5 micrograms of RNA at 0.5 mg/ml in water and 1 microgram of protamine at 0.5 mg/ml in pure water (resulting in approximately 120 nm protamine-RNA nanoparticles) were put in wells of a round bottom 96-well plate. Eventually, 3 microliters of non-salty (glucose 10%, fructose 10%, mannose 10%) or salty (PBS) solutions were added and left 10 minutes at room temperature before addition of 200 microliters of PBMCs. These cells were prepared from a healthy human donor using Ficoll® gradient separation. They were then washed with PBS and resuspended at 5 million per ml in RPMI with 10% fetal calf serum plus penicillin and streptomycin. As negative control, PBMCs were cultured alone.

These preparations were incubated for 18-24 hours at 37° C. with 5% $CO_2$. Then, the supernatants of the cultures were collected. The content of IFN-alpha and TNF-alpha in these supernatants was evaluated using 20 or 10 microliters of supernatants and ELISA kits from Mabtech pan-interferon-alpha and Biolegend TNF-alpha. The results are presented in FIG. 2A in pg/ml in the cell culture supernatants. They demonstrate that the specific immunostimulating properties of small (less than 450 nm) particles, i.e induction of interferon-alpha in PBMCs, is preserved when the particles are formulated in isotonic non-salty sugar-based solutions, but lost when salts (i.e. in the form of PBS) are added. In the presence of salts, particles get larger and thereby induce TNF-alpha in PBMCs. Thus, to preserve the size and linked immunostimulating characteristics of protamine-RNA particles, the isotonic formulation for injection has to contain no salt (or a low salt concentration) and a non-electrolyte osmotic agent, such as sugar.

Example 3: Translatability of Protamine-RNA Nanoparticles is Preserved in 5% Sugar Formulations Six microliters of a mixture containing 1 microgram of mRNA (coding for firefly luciferase) at 0.5 mg/ml in pure water and 2 micrograms of protamine at 0.5 mg/ml in water (i.e. approximately 120 nm protamine-RNA nanoparticles) were put in wells of a white flat bottom 96-well plate. Eventually, 6 microliters of non-salty (glucose 10%, fructose 10%, mannose 10%) or salty (PBS or Ringer Lactate) solutions were added and left 10 minutes at room temperature before addition of 100 microliters of HEK cells (2 million cells per milliliter) in RPMI with 10% fetal calf serum plus penicillin and streptomycin. As negative control, HEK cells were cultured alone.

These preparations were incubated for 18-24 hours at 37° C. with 5% $CO_2$. Then, 75 microliters of Bright Glo™ (Promega) were added. Thereby the expression of luciferase from the mRNA entrapped in the particles could be measured. The results are presented in FIG. 2B. They demonstrate that the capacity of releasing RNA (here mRNA) into the cytosol and making it available for translation, which is higher for small (less than 450 nm) than for large (above 450 nm) protamine-RNA particles, is preserved when the particles are formulated in isotonic non-salty sugar-based solutions, but lost when salts (PBS or Ringer Lactate) are added. In the presence of salts, particles get larger over time and thereby, as do larger nanoparticles (above 450 nm), less efficiently release free cytosolic RNA in the cytosol, which leads to reduced luciferase activity. Thus, to preserve the size and linked optimal translation characteristics of protamine-RNA nanoparticles (i.e release of encapsulated RNA), the isotonic formulation for injection has to contain very low salt concentrations.

Example 4: Immunostimulating Capacities of Protamine-RNA Nanoparticles are Preserved in 1% to 20% Glucose Three microliters of a mixture containing 0.5 micrograms of RNA at 0.5 mg/ml in water and 1 microgram of protamine at 0.5 mg/ml in pure water (i.e. approximately 120 nm protamine-RNA nanoparticles) were put in wells of a round bottom 96-well plate. Eventually, 3 microliters of 2% or 5% or 10% or 20% or 40% glucose or PBS solutions were added and left 10 minutes at room temperature before addition of 200 microliters of PBMCs. These cells were prepared from a healthy human donor using Ficoll® gradient separation. They were then washed with PBS and resuspended at 5 million per ml in RPMI with 10% fetal calf serum plus penicillin and streptomycin. As negative control, PBMCs were cultured alone.

These preparations were incubated for 18-24 hours at 37° C. with 5% $CO_2$. Then, the supernatants of the cultures were collected. The content of IFN-alpha and TNF-alpha in these supernatants was evaluated using 20 or 10 microliters of supernatants and ELISA kits from Mabtech pan-interferon-alpha and Biolegend TNF-alpha. The results are presented in FIG. 3A in pg/ml in the cell culture supernatant. They demonstrate that the specific immunostimulating properties of small (less than 450 nm) particles, i.e induction of interferon-alpha in PBMCs, is preserved when the particle solution contains glucose at a final concentration of from 1% to 20% but lost when salts (final concentration: 0.5×PBS) are added. In the presence of salts, particles get larger and thereby induce TNF-alpha in PBMCs. Thus, glucose at final concentrations ranging from 1% to 20% can be used to preserve the size and linked immunostimulating characteristics of protamine-RNA particles.

Example 5: Translatability of Protamine-RNA Nanoparticles is Preserved in 1% to 20% Glucose Six microliters of a mixture containing 1 microgram of mRNA (coding for firefly luciferase) at 0.5 mg/ml in water and 2 micrograms of protamine at 0.5 mg/ml in pure water (i.e. approximately 120 nm protamine-RNA nanoparticles) were put in wells of a white flat bottom 96-well plate. Eventually, 6 microliters of 2% or 5% or 10% or 20% or 40% glucose or PBS solutions were added and left 10 minutes at room temperature before addition of 100 microliters of HEK cells (2 million cells per milliliter) in RPMI with 10% fetal calf serum plus penicillin and streptomycin. As negative control, HEK cells were cultured alone.

These preparations were incubated for 18-24 hours at 37° C. with 5% $CO_2$. Then, 75 microliters of Bright Glo™ (Promega) were added. Thereby the expression of luciferase from the mRNA entrapped in the particles could be measured. The results are presented in FIG. 3B. They demonstrate that the capacity of releasing RNA into the cytosol and making it available for translation, which is higher for small (less than 450 nm) than for large (above 450 nm) protamine-RNA particles, is preserved when the particles are formulated in 1% to 20% sugar-based solutions, but diminished when salts (e.g. PBS) are added. In the presence of salts, particles get larger over time and thereby, as do larger nanoparticles (above 450 nm), less efficiently release free cytosolic RNA into the cytosol as shown by the reduced luciferase activity. Thus, to preserve the size and linked optimal translatability of protamine-RNA nanoparticles, the formulation for injection should contain no salt (or very low salt concentrations) and, instead, 1% to 20% sugar.

Figure 4A:
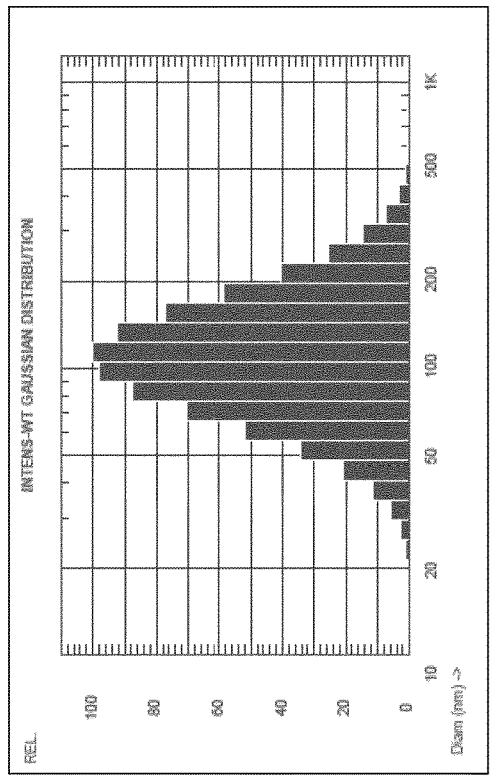
Figure 4A:
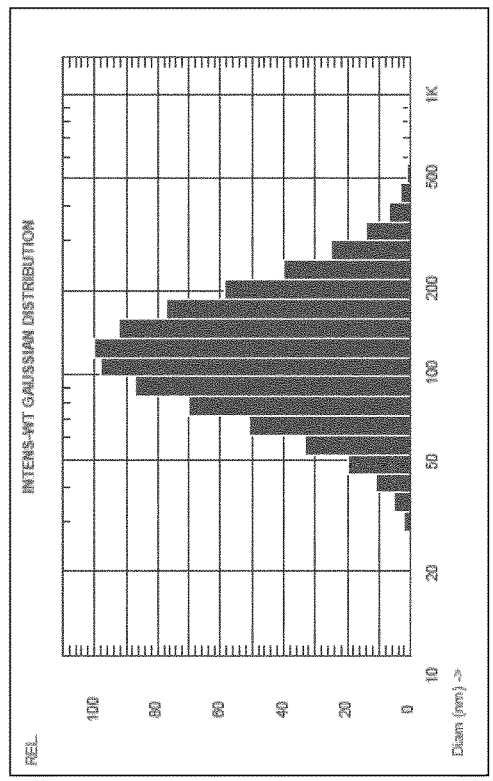
Figure 4B:
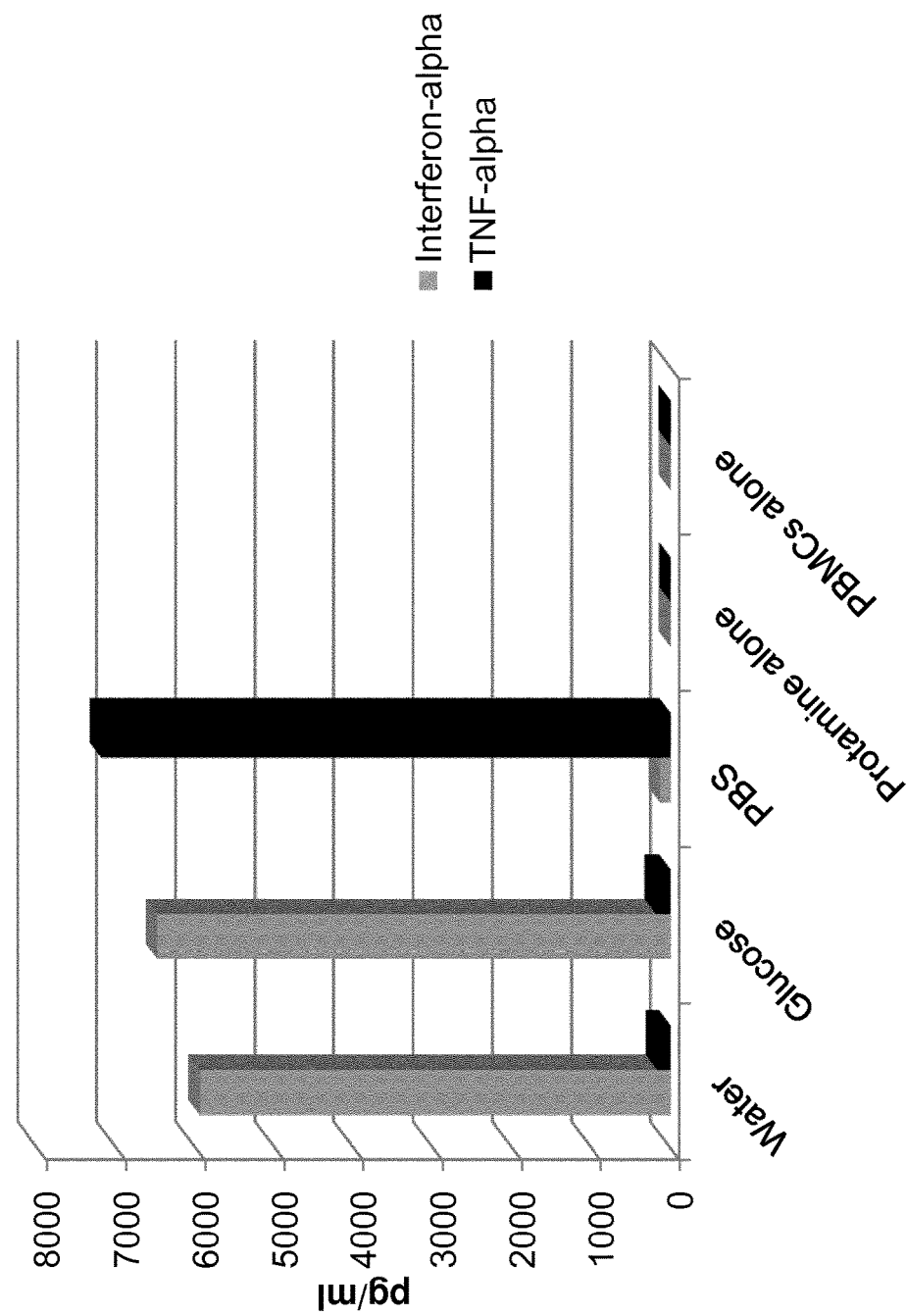
Figure 4C:
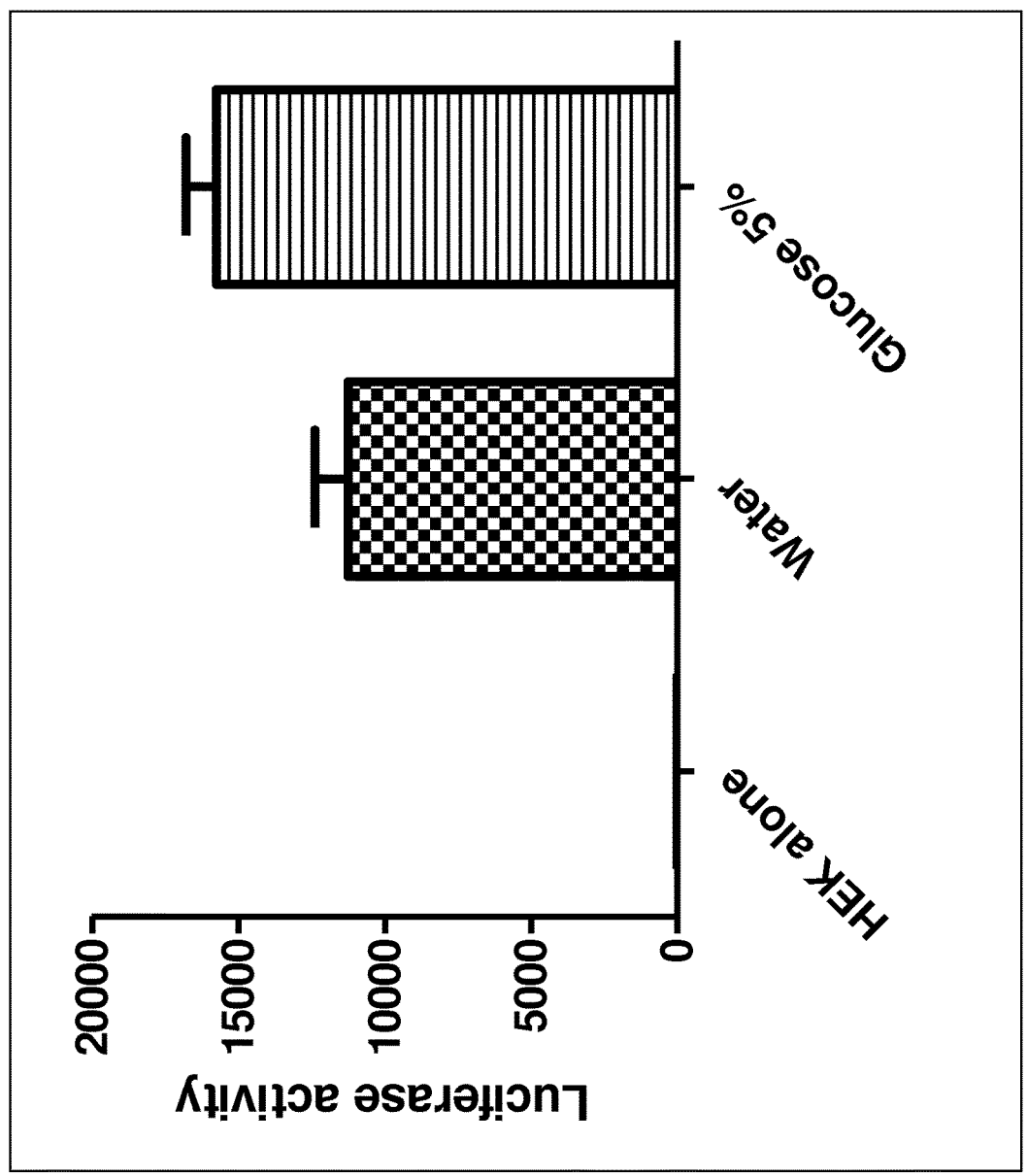

Example 6: Stable Protamine-RNA Nanoparticles of Less than 450 nm can be Generated by Mixing RNA and Protamine Each Diluted in 5% Glucose Eight micrograms of mRNA coding for luciferase were diluted to 0.5 mg/ml in water and mixed with 16 micrograms of Protamin® IPEX 5000 diluted at 0.5 mg/ml in water. After 10 minutes, volume was filled up to 200 microliters using 152 microliters 5% glucose. Light scattering spectroscopy measurement of particles after 10 minutes at room temperature indicated a mean size of 123.3 nm as depicted in FIG. 4A. When particles were made by mixing 8 micrograms of mRNA encoding luciferase diluted at 0.5 mg/ml in 5% glucose and 16 micrograms of Protamin® IPEX 5000 diluted at 0.5 mg/ml in 5% glucose (incubation 10 minutes, addition of 152 microliters 5% glucose and measurement using light scattering spectroscopy), a similar type of particles with a mean diameter of 135.6 nm was generated. Thus, the size of particles made by mixing RNA and protamine diluted to 0.5 mg/ml in water or RNA and protamine diluted to 0.5 mg/ml in 5% glucose was equivalent. This means that protamine-RNA particles in solutions approaching physiological isotonicity (approximately 300 mOsm/L) can be obtained by either adding glucose to particles formed by reagents diluted in water or by diluting reagents (RNA and protamine) in 5% glucose before mixing them.

Example 7: Diluting Protamine and RNA in Water or 5% Glucose Generates Particles with Similar Immunostimulating Capacities mRNA coding for firefly luciferase was diluted to 0.5 mg/ml in pure water or in 5% glucose or in PBS. Protamin® IPEX 5000 was diluted to 0.5 mg/ml in pure water or in 5% glucose or in PBS. Water-diluted protamine and RNA were mixed together generating "water" particles; glucose-diluted protamine and RNA were mixed together generating "glucose" particles; PBS-diluted protamine and RNA were mixed together generating "PBS" particles. The mixtures were all incubated at room temperature for 10 minutes. Then they were distributed to wells of a U-bottom 96-well plate (3 microliters per well equivalent to 0.5 micrograms RNA and 1 microgram protamine) before two hundred microliters (1 million cells) of human Peripheral Blood Mononuclear Cells (PBMCs obtained by centrifugation of fresh human blood on a ficoll solution) in complete culture medium (RPMI containing 10% fetal calf serum, glutamine and penicillin/streptomycin) were added. As negative control, PBMCs were cultured alone or in the presence of 1 microgram of protamine. After 18 hours at 37° C. in a humidified atmosphere containing 5% $CO_2$, the amount of interferon-alpha and TNF-alpha produced by cells was evaluated using 20 microliters and 10 microliters, respectively, of the culture supernatants and the Mabtech pan-interferon-alpha and Biolegend TNF-alpha kits. "Water" and "glucose" particles which are equivalent in size (see FIG. 4A) had similar immunostimulating characteristics: they induced interferon-alpha production in PBMCs. Thus, an isotonic solution of small (less than 450 nm) immunostimulating protamine-RNA nanoparticles can be generated by mixing protamine and RNA both diluted in 5% glucose.

Example 8: Diluting Protamine and RNA in Water or 5% Glucose Generates Particles with Similar Translatability mRNA coding for firefly luciferase was diluted to 0.5 mg/ml in pure water or in 5% glucose. Protamin® IPEX 5000 was diluted to 0.5 mg/ml in pure water or in 5% glucose. Water-diluted protamine and RNA were mixed together generating "water" particles; glucose-diluted protamine and RNA were mixed together generating "glucose 5%" particles. The mixtures were incubated at room temperature for 10 minutes. Then they were distributed to wells of a flat-bottom white 96-well plate (6 microliters per well equivalent to 1 microgram RNA and 2 micrograms protamine) before one hundred microliters (0.2 million cells) of HEK cells in complete culture medium (RPMI containing 10% fetal calf serum, glutamine and penicillin/streptomycin) were added. As negative control, HEK cells were cultured alone. These preparations were incubated for 18-24 hours at 37° C. with 5% $CO_2$. Then, 75 microliters of Bright Glo™ (Promega) were added. Thereby, the expression of luciferase from the mRNA entrapped in the particles could be measured. "Water" and "glucose 5%" particles which were equivalent in size (see FIG. 4A) had similar translation characteristics. Thus, an isotonic solution of small (less than 450 nm) translatable protamine-RNA nanoparticles can be generated by mixing protamine and RNA both diluted in 5% glucose.

The invention claimed is:

1. An aqueous injection formulation comprising:
   (a) particles containing protamine and RNA, wherein the particles have an average size in the range of from 10 to 450 nm as determined by dynamic light scattering, and
   (b) 4 to 6% (w/v) of glucose,
   wherein the aqueous injection formulation comprises less than 10 mM electrolytes.

2. The aqueous injection formulation of claim 1, wherein the aqueous injection formulation comprises 5% (w/v) of glucose.

3. The aqueous injection formulation of claim 1, wherein the particles have a polycation:RNA mass ratio in the range of from 16:1 to 1:2, preferably in the range of from 8:1 to 1:2, more preferably in the range of from 4:1 to 1:2.

4. The aqueous injection formulation of claim 1, wherein the particles have an average size in the range of from 30 to 450 nm or 50 to 450 nm, as determined by dynamic light scattering.

5. The aqueous injection formulation of claim 1, wherein the RNA is selected from the group consisting of messenger RNA (mRNA), transfer RNA (tRNA), ribosomic RNA (rRNA), small nuclear RNA (snRNA), small inhibitory RNA (siRNA), small hairpin RNA (shRNA), microRNA (miRNA), antisense RNA, immunostimulating RNA (isRNA) and RNA aptamers, preferably from the group consisting of mRNA, siRNA, shRNA, miRNA, antisense RNA, isRNA and RNA aptamers.

6. The aqueous injection formulation of claim 1 being suitable for parenteral administration.

7. A pharmaceutical composition or kit comprising the aqueous injection formulation of claim 1.

8. The aqueous injection formulation of claim 1 for use in a method of treatment or prevention of a disease or for use in a method of immunostimulation.

9. A method for physically stabilizing particles comprising a polycation and RNA, wherein the polycation is protamine, the method comprising formulating the particles in an aqueous formulation comprising:
   (a) particles containing protamine and RNA, wherein the particles have an average size in the range of from 10 to 450 nm as determined by dynamic light scattering, and
   (b) 4 to 6% (w/v) of glucose,
   wherein the aqueous injection formulation comprises less than 10 mM electrolyte.

10. The method of claim 9, wherein physically stabilizing comprises reducing or preventing enlargement of the particles over time.

* * * * *